United States Patent
Cho et al.

(10) Patent No.: US 9,868,828 B2
(45) Date of Patent: Jan. 16, 2018

(54) DEFINED THREE-DIMENSIONAL MICROENVIRONMENT FOR STEM CELL

(71) Applicants: AMOLIFESCIENCE CO., LTD., Seoul OT (KR); Konkuk University Industrial Cooperation Corp., Seoul (KR)

(72) Inventors: Ssang-Goo Cho, Seoul (KR); Kyuwon Baek, Seoul (KR); Gwang-Mo Yang, Seoul (KR); Chan Kim, Gwangju (KR); Jihye Won, Seongnam-si (KR); In Yong Seo, Seoul (KR); Dong-Sik Seo, Incheon (KR); Chulbae Yoo, Bucheon-si (KR); Hui-Gwan Goo, Seoul (KR); Seonho Jang, Seoul (KR); Song Hee Koo, Seoul (KR); Sang-Eun Park, Suwon-si (KR)

(73) Assignees: AMOLIFESCIENCE CO., LTD., Seoul (KR); KONKUK UNIVERSITY INDUSTRIAL COOPERATION CORP., Seoul (KR)

( * ) Notice: Subject to any disclaimer, the term of this patent is extended or adjusted under 35 U.S.C. 154(b) by 0 days.

(21) Appl. No.: 15/191,406

(22) Filed: Jun. 23, 2016

(65) Prior Publication Data
US 2016/0377600 A1 Dec. 29, 2016

Related U.S. Application Data

(60) Provisional application No. 62/183,663, filed on Jun. 23, 2015.

(51) Int. Cl.
| | | |
|---|---|---|
| *C08J 3/28* | (2006.01) | |
| *C12N 5/0735* | (2010.01) | |
| *C12N 5/074* | (2010.01) | |
| *C08L 33/20* | (2006.01) | |
| *C12N 5/00* | (2006.01) | |

(52) U.S. Cl.
CPC .......... *C08J 3/28* (2013.01); *C08L 33/20* (2013.01); *C12N 5/0068* (2013.01); *C12N 5/0606* (2013.01); *C12N 5/0696* (2013.01); *C08J 2327/16* (2013.01); *C08J 2333/20* (2013.01); *C08J 2427/16* (2013.01); *C08J 2433/20* (2013.01); *C12N 2533/30* (2013.01); *C12N 2535/00* (2013.01)

(58) Field of Classification Search
CPC ...... C08J 3/28; C08J 2333/20; C08J 2427/16; C08J 2433/20; C08J 2327/16; C08L 33/20; C12N 5/0068; C12N 5/0606; C12N 5/0696; C12N 2535/00; C12N 2535/30
See application file for complete search history.

(56) References Cited

U.S. PATENT DOCUMENTS

| | | | | |
|---|---|---|---|---|
| 2001/0007662 A1* | 7/2001 | Knepp | ................. | A61K 9/0019 424/198.1 |
| 2006/0200232 A1* | 9/2006 | Phaneuf | .............. | B29C 47/0021 623/1.42 |
| 2009/0221047 A1* | 9/2009 | Schindler | ............... | B01D 39/04 435/160 |
| 2010/0303881 A1* | 12/2010 | Hoke | ...................... | A61K 9/70 424/423 |
| 2011/0038936 A1* | 2/2011 | Griswold | ............. | A61K 9/0092 424/486 |
| 2015/0216998 A1* | 8/2015 | Feinstein | ......... | A61K 47/48823 424/450 |
| 2015/0306276 A1* | 10/2015 | Shimp | .................... | A61L 27/24 424/422 |
| 2015/0344525 A1* | 12/2015 | Luo | ...................... | A61K 9/5169 424/9.6 |

OTHER PUBLICATIONS

Miyamoto, "Integrins Can Collaborate with Growth Factors for Phosphorylation of Receptor Trosine Kinases and MAP Kinase Activation: Roles of Integrin Aggregation and Occupancy of Receptors," The Journal of Cell Biology, 1996.
Li, et al., "Agonists of Fibroblast Growth Factor Receptor Induce Neurite Outgrowth and Survival of Cerebellar Granule Neurons", Dev. Neurobiol. (2009), 69(13):837-54.
Lampe, et al., "Building stem cell niches from the molecule up through engineered peptide materials", Neuroscience Letters (2012) 519:138-146.
Annabi et al., "Controlling the Porosity and Microarchitecture of Hydrogels for Tissue Engineering", Tissue Eng. Part B (Rev. 2010), 16(4):371-83.
Mori et al. "Crosstalk between Fibroblast Grownth Factor (FGF) Receptor and Integrin through Direct Integrin Binding to FGF and Resulting Integrin-FGF-FGFR Temary Complex Formation", Med. Sci., (2013).
Mori et al., "Direct binding of Integrin v 3 to FGF1 Plays a role in FGF1 Signaling", J. Biol. Chem. (2008), 283:18066-18075.
Li, et al., "Fibroblast growth factor-derived peptides: functional agonists of the fibroblast growth factor receptor", J. Neurochem. (2008) Feb., 104(3):667-82.
Legate, et al., "Genetic and cell biological analysis of integrin outside-in signaling", Genes Dev. (2009), 23:39x 418).
Rider "Heparin/heparan sulphate binding in the TGF-beta cytokine superfamily", Biochem. Soc. Trans. (2006) 34:458-460.
Olsen et al. "Insights into the molecular basis for fibroblast growth factor receptor autoinhibition and ligand binding promiscuity" , Proc. Natl Acad. Sci. (2004) 101:935-940).
Li, et al., "Neuritogenic and Neuroprotective Properties of Peptide Agonists of the Fibroblast Growth Factor Receptor", Int. J. Mol. Sci. 2010, 11(6):2291-2305).
Manfe, et al., Peptides derived from specific interaction sites of the fibroblast growth factor 2—FGF receptor complexes induce receptor activation and signaling, J. Neurochem. 2010, 114(1):74-86).

(Continued)

*Primary Examiner* — Robert Jones, Jr.
(74) *Attorney, Agent, or Firm* — TraskBritt

(57) ABSTRACT

This disclosure provides for a three-dimensional (3D) microenvironment presenting defined physical or mechanical cues that regulate cellular behavior and use of the matrix. The disclosure also provides for devices and methods for screening for optimal combinations of physical and mechanical cues in order to create a microenvironment that can regulate specific cellular behavior such as cell growth, proliferation, migration or differentiation.

8 Claims, 15 Drawing Sheets

(56) References Cited

OTHER PUBLICATIONS

T. Miyazaki, et al., "Recombinant human laminin isoforms can support the undifferentiated growth of human embryonic stem cells", Biochem. Biophys. Res. Commun. (2008), 375:2x 32.

Braam et al., "Recombinant vitronectin is a functionally defined substrate that supports human embryonic stem cell self-renewal via alphavbeta5 integrin", Stem Cells (2008), 28:2257-2265).

Bell et al. "Rotational Coupling of the Transmembrane and Kinase Domains of the Neu Receptor Tyrosine Kinase", Mol. Biol. of the Cell, (2000) 11:3589-3599.

Lutolf et al. "Synthetic biomaterials as instructive extracellular microenvironments for morphogenesis in tissue engineering", Nature Biotechnology (2005) 23 (1):47-55).

Melkoumian et al., Synthetic peptide-acrylate surfaces for long-term self-renewal and cardiomyocyte differentiation of human embryonic stem cells, Nat. Biotechnol. (2010).

O'Brien, et al., "The Effect of Pore Size on Cell Adhesion in Collagen-GAG Scaffolds", RCSI (2005); 26(4):433-41.

Cattavarayan, et al., "a6β1- and av-integrins are required long-term self-renewal of murine embryonic stem cells in the absence of LIF, BMC" Cell Biology (2015), 16:3.

J. Li, et al., "MEK/ERK signaling contributes to the maintenance of human embryonic stem cell self-renewal, Differentiation" (2007), 75:299-307).

Meng, et al., "Characterization of integrin engagement during defined human embryonic stem cell culture", FASEB J. (2010), 24(4):1056-65.

Mercier et al. "Anatomy of the brain neurogenic zones revisited: fractones and the fibroblast/macrophage network", J. Comp. Neurol. (2002) 451:170-188.

Schwartz et al, "Interactions between mitogenic stimuli or a thousand and one connections" Curr. Opin. Cell Biol. 11:197-202 (1999).

Yamada et al. "Integrin signaling, in Signaling Networks and Cell Cycle Control" (ed. J.S. Gutkind) 1-25 (Humana Press, Totowa, NJ, 2000).

* cited by examiner

DEFINED THREE-DIMENSIONAL MICROENVIRONMENT FOR STEM CELL

CROSS-REFERENCE TO RELATED APPLICATION

This application claims the benefit of U.S. Provisional Patent Application Ser. No. 62/183,663, filed Jun. 23, 2015, the disclosure of which is hereby incorporated herein in its entirety by this reference.

TECHNICAL FIELD

This disclosure relates to a defined three-dimensional microenvironment for stem cells.

BACKGROUND

Increasing evidence has demonstrated that a local microenvironment, stem cell niche, is important in regulating their self-renewal and differentiation in tissue and organ development process. Stem cell niche provides a complex array of biochemical and physical cues in a spatiotemporally defined fashion, engaging and instructing stem cells to proliferate migrate and differentiate.

Such microenvironment consists of many factors including extracellular matrices (ECMs), growth factors, signaling molecules, etc. Although biochemical cues including soluble factors such as FGFs, BMPs and Wnts have been well studied for their role in regulating stem cell behavior, the effect of cell-matrix interaction in stem cell development is poorly understood.

Recapitulating the stem cell niche is a critical goal of regenerative medicine. Ideally, an engineered stem cell niche would include both spatial organization and dynamic modulation of cells, soluble factors, and matrix. While biomaterials technologies are being developed to address these needs, currently available matrices often lack this level of complexity. (See Kyle J. Lampe, et al., Building stem cell niches from the molecule up through engineered peptide materials, *Neuroscience Letters* (2012) 519:138-146; and M. P. Lutolf and J. A. Hubbell, Synthetic biomaterials as instructive extracellular microenvironments for morphogenesis in tissue engineering, *Nature Biotechnology* (2005) 23 (1):47-55.)

Many attempts have been made to create a synthetic stem cell niche by incorporating cell adhesion ligands into nanofiber or hydrogel-based scaffolds. For example, nanofiber-based scaffolds have been investigated for the regeneration of connective tissues, such as bone, meniscus, intervertebral disk, cartilage, tendons and ligaments. Nano-scale fibers have been shown to direct cell attachment and matrix deposition and represent an ideal system to model the collagenous matrices present within native tissue structures. These scaffolds exhibit high aspect ratio, surface area, permeability and porosity, and can be fabricated from a variety of polymers, both natural and synthetic, with tunable fiber diameter and matrix alignment.

A biochemically, mechanically and physically engineered nanofibrous microenvironment has been developed that mimics native extracellular microenvironments by presenting controlled fiber diameter, topography, pore size and elasticity of a matrix, as well as bioactive peptide motifs derived from extracellular matrix proteins on the nanofiber. Our engineered microenvironment can be used as an array of cell culture environments for screening of cell culture or tissue engineering environment by elucidating or regulating cellular behaviors such as cell adhesion, migration, growth, proliferation or morphogenesis as evidenced in stem cell assays.

BRIEF SUMMARY

The disclosure is directed to a three-dimensional nanofiber-based stem cell niche comprising a plurality of synthetic or natural polymer.

BRIEF DESCRIPTION OF DRAWINGS

The patent or application file contains at least one drawing executed in color. Copies of this patent or patent application publication with color drawing(s) will be provided by the Office upon request and payment of the necessary fee.

These and other features and advantages of the disclosure are evident from the following embodiments when read in conjunction with the accompanying drawings in which.

DETAILED DESCRIPTION

Figure 1:
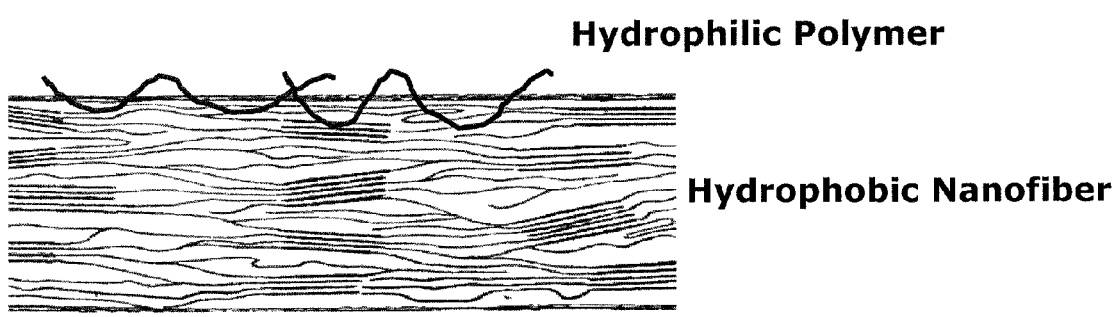
FIG. 1 shows the schematic representation of a synthetically designed nanofibrous extracellular matrix 3D microenvironment.

This disclosure is directed to physically and mechanically defined microenvironments that mimic natural extracellular microenvironments.

In one aspect, an extracellular microenvironment surface that induces integrin signaling to promote signal pathway for self-renewal or proliferation of pluripotent stem cell in serum- or feeder-free conditions is provided. It is well known that integrin signaling involves Erk activation and self-renewal of embryonic stem cell is mediated signal through Ras-Raf-MEK-Erk cascade.

As used herein, "microenvironment" refers to physical and/or biochemical cues, surrounding a cell in an organism or in the laboratory. Physical cues refer to the physical or mechanical properties of a substrate surrounding the cell. For example, diameter or pore of the substrate is the physical cues. Molecules, including small molecules such as compounds and soluble factors, macromolecules such as insoluble polymers, nutrients, growth factors, fluids, cytokines and parameters such as pH, ionic strength and gas composition, and the like surrounding the cell are the biochemical cues. The molecules may be, reversibly or irreversibly in response to biological or physiological conditions, immobilized to the substrate.

This disclosure provides an electroprocessable composition to engineer an extracellular microenvironment presenting controlled physical and/or mechanical cues.

Electroprocess including electrospinning or electrospraying is a means of producing fibers or particles with diameters generally between 10 to 1,000 nanometers. It has the ability to produce fibers or particles that are far smaller than those produced by conventional means such as wet spinning or melt spinning.

This disclosure provides a physical or mechanical microenvironment comprised of an electroprocessed composition presenting at least one or more hydrophilic component that supports cellular behavior such as cell adhesion, migration, or growth.

In one aspect, the disclosure provides an electrospinnable composition for a fibrous microenvironment comprised of two components, hydrophilic component and a structural component. In one embodiment, a structural component is a polymer to provide physical or mechanical cues such as pore size or elasticity, whereas hydrophilic component contains extracellular component.

Any electrospinnable polymer, natural or synthetic, for use in this disclosure can be a structural component. Preferably, an electrospinnable polymer is a synthetic polymer that has the appropriate viscosity in solution. Any polymer meeting the above requirements is useful herein, and the selection of the specific polymer and acquisitions or preparation of such polymer would be conventionally practiced in the art (see reference here). Preferably, such electrospinnable polymers are selected from groups comprising polyvinylidene fluoride (PVDF), polyacrylonitrile (PAN), polyethersulfone (PES), polylactic acid (PLA), polyglycolic acid (PGA), poly (lactide-glycolic) acid (PLGA), polycaprolactone, poly(alkylene oxides), particularly poly(ethylene glycols), poly(vinyl alcohols), polypeptides, poly(amino acids), such as poly(lysine), poly(allylamines) (PAM), poly (acrylates), polyesters, polyphosphazenes, pluronic polyols, polyoxamers, poly(uronic acids) and copolymers, including graft polymers thereof.

In another aspect, the disclosure provides a nanofibrous matrix to mimic a natural extracellular microenvironment, wherein the matrix has an elastic or linear modulus of about 0.5 kPa to about 1 MPa and fiber diameter of about 50 nm to 1,000 nm. In one embodiment, the method to making the nanofibrous matrix includes (a) generating an electrostatic field between a first electrode and a second electrode; and (b) electrospinning a solution of composition comprising the hydrophilic component and a synthetic polymer as a structural component onto a collection surface located between the first electrode and the second electrode to provide a plurality of nanofibers on the collection surface.

The structural polymer may be selected to have a wide range of molecular weights, generally from as low as 100,000 up to millions of Daltons. Preferably, the selected polymer has a molecular weight of less than about 300,000 to 500,000.

In another embodiment, a hydrophobic polymer is used to form an electrospinnable composition wherein PVDF, PAN, and/or PES, alone or in combination, has a molecular weight of from about 50 Kda to about 500 kDa. In one embodiment, the fiber includes about 0.1 weight percent mussel adhesive protein and about 10 weight percent hydrophobic polymer.

In another embodiment, a hydrophilic component is used to modify an electrospinnable composition wherein natural or synthetic polymer such as extracellular matrix mimetic protein, polyvinyl pyrrolidone (PVP) or polyethylene glycol (PEG) having a molecular weight of from about 30 kDa to about 300 kDa can be used to modify the composition.

In one embodiment of this disclosure, a 3D nanofibrous microenvironment having 200 nm and 700 nm diameter, respectively, are provided to support self-renewal and proliferation of murine embryonic stem cell.

This disclosure provides a nanofibrous microenvironment having elasticity that can be readily controlled by adjusting the weight ratio in hydrophilic component, whereas physical cues such as pore size and biochemical cues are constant.

In one embodiment, compositions are provided to engineer microenvironment having elasticity from 1 kPa to 1 MPa, whereas average pore size is constant and constant biochemical cues. The average pore size can range from 50 nm to 10 μm.

Pore size of a scaffold can affect cell behavior within a scaffold and that subtle changes in pore size can have a significant effect on cell behavior such as cell migration. The porosity and pore architecture in terms of porosity and pore architecture play a significant role in cell survival, proliferation, and migration, and thus they are key elements to design a synthetic three-dimensional microenvironment. (N. Annabi et al., Controlling the Porosity and Microarchitecture of Hydrogels for Tissue Engineering, *Tissue Eng. Part B Rev.* 2010, 16(4):371-83). The porosity of a hydrogel depends on PEG molecular weight, concentration, acidity, gelation temperature and gelation time.

If the pores become too large, the mechanical properties of the scaffold will be compromised due to void volume and, as pore size increases further, the specific surface area will eventually reduce to a level that will limit cell adhesion.

As summarized in Table 2, the optimal pore size will vary with different cell types (F. J. O'Brien, et al., The effect of pore size on cell adhesion in collagen-GAG scaffolds, *Biofunctionals* 2005; 26(4):433-41).

TABLE 1

Optimal pore size for cell infiltration and host tissue ingrowth

| Cell/tissue type | Pore size (μm) | Scaffold material |
|---|---|---|
| Human skin fibroblasts | <160 μm | PLA/PLG |
| Bone | 450 μm | PMMA |
| Fibrocartilaginous tissue | 150-300 μm | Polyurethane |
| Adult mammalian skin cells | 20-125 μm | Collagen -GAG |
| Osteogenic cells | 100-150 μm | Collagen-GAG |
| Smooth muscle cells | 60-150 μm | PLA |
| Endothelial cells | <80 μm | Silicon nitride |

This disclosure provides a nanofibrous microenvironment presenting biochemical cues to regulate stem cell fate by immobilizing signaling cues that allows for generation of persistent gradients of biomolecules including extracellular matrix proteins, growth factors, or cytokines in a spatiotemporally defined manner.

It has been known that cross-talk between integrins and growth factor receptors by two mechanism, i) two separate signals merge with one another in multiple levels inside the cells (see Legate, et al., Genetic and cell biological analysis of integrin outside-in signaling, Genes Dev. 2009, 23:397-418), or ii) FGF1 directly binds to integrin $\alpha v \beta 3$ and induces the FGFR1-FGF1-integrin $\alpha v \beta 3$ ternary complex (S. Mori et al., Direct binding of integrin $\alpha v \beta 3$ to FGF1 plays a role in FGF1 signaling, J. Biol. Chem. 2008, 283:18066-18075).

In one embodiment, the extracellular microenvironment surface to activate integrin $\alpha 5 \beta 1$ and/or integrin $\alpha 6 \beta 1$-mediated signaling at the same time is provided for self-renewal and proliferation of pluripotent or multi-potent stem cell.

A biochemical cue such as ECM protein or growth factors can be a natural or recombinant extracellular matrix protein, ECM-derived domain including core motif that binds to specific integrin or its mimetic, growth factor, GF-derived domain containing core motif that bind to specific binding sites of such growth factor receptor, or its mimetic. The mimetic comprises a recombinant protein or polypeptide functionalized with at least one or more peptide motifs derived from a variety of extracellular matrix proteins or growth factors.

Any suitable natural extracellular matrix proteins including, but not limited to, fibronectin, laminin, vitronectin, may be used as an extracellular component to activate integrins. Preferably, the extracellular matrix protein is fibronectin. More preferably, the fibronectin can be used alone or in combination with laminin, vitronectin or cadherin.

Any suitable natural growth factors are fibroblast growth factor (FGF) or transforming growth factor (TGF) may be used as an extracellular component to activate such growth factor receptors. Preferably, the growth factor can be used alone or in combination with FGF and TGF.

Generally, any extracellular mimetic component including extracellular matrix mimetic or growth factor mimetic comprises a substrate protein recombinantly or chemically functionalized with peptide motif derived from extracellular matrix proteins or growth factors.

Any suitable substrate protein including, but not limited to, fibrin, elastin, mussel adhesive protein may be used as the substrate protein to present extracellular component. Preferably, the protein is a recombinant mussel adhesive protein.

Any suitable recombinant mussel adhesive protein may be used as the extracellular component in this disclosure. Examples of commercially available substrate proteins include MAPTrix™ ECM marketed by Kollodis BioSciences, Inc. (North Augusta, S.C.). An optional third component is a biocompatible polymer (e.g., polyethylene glycol or polyvinylalcohol), which may be added to the compositions to enhance their physicomechanical characteristics such as physical or mechanical properties of a customizable microenvironment.

The MAPTrix™, developed by Kollodis BioSciences, Inc. (North Augusta, S.C.), are predesigned mussel adhesive protein or barnacle-based extracellular component mimetics. The mussel adhesive proteins were recombinantly functionalized with a variety of ECMs-, GFs-, or other ligand-derived peptides in order to mimic the bioactivity of naturally occurring ligands such as ECMs, GFs, or other soluble factors such as cytokines, including IL-3 or LIF, which were demonstrated to have a similar bioactivity to natural or recombinant ECMs, GFs, or soluble factors in primary cell cultures as compared to various natural or recombinant ECM, GF or cytokine proteins. The pre-designed MAPTrix™ mimetics are highly advantageous for creating extracellular microenvironments. For example, it provides for the design of cell-specific or user-defined regulation of extracellular microenvironments to emulate the native microenvironment in terms of biochemical cues.

The MAPTrix™ is a fusion protein comprising a first peptide of mussel foot protein FP-5 that is selected from the group consisting of SEQ ID NOS:1-4, or barnacle-derived adhesive protein consisting of SEQ ID NO:5 and a second peptide of at least one selected from the group consisting of mussel FP-1 selected from the group consisting of SEQ ID NOS:6-8, mussel FP-2 (SEQ ID NO:9), mussel FP-3 selected from the group consisting of SEQ ID NOS:10-11, mussel FP-4 (SEQ ID NO:12), mussel FP-6 (SEQ ID NO:13) and fragment thereof, and the second peptide is linked to C-terminus, N-terminus or C- and N-terminus of the FP-5. Preferably, the second peptide is the FP-1 comprising an amino acid sequence of SEQ ID NO:6.

Extracellular components including integrin binding motif or growth factor receptor binding motif such as fibroblast growth factor (FGF) and transforming growth factor (TGF)-derived peptide motif, WNT and/or LIF (leukemia inhibitor factor) may also be incorporated into the mussel adhesive protein to further enhance the beneficial effect of the extracellular environment mimic on self-renewal and pluripotency of a stem cell.

There are 24 known integrin heterodimers comprised of one of eighteen $\alpha$ subunits and one of eight $\beta$ subunits and these have a diverse range of functions mediating cell-cell adhesion, growth factor receptor responses and intracellular signaling cascades for cell migration, differentiation, survival and proliferation. A number of ECM molecules or domains are capable of assisting in the maintenance of undifferentiated hESC alone or in combination, including laminin 511 (see T. Miyazaki, et al., Recombinant human laminin isoforms can support the undifferentiated growth of human embryonic stem cells, Biochem. Biophys. Res. Commun. (2008), 375:27-32), fibronectin and vitronectin (see Melkoumian et al., Synthetic peptide-acrylate surfaces for long-term self-renewal and cardiomyocyte differentiation of human embryonic stem cells, Nat. Biotechnol. (2010), 28:606-610; Braam et al., Recombinant vitronectin is a functionally defined substrate that supports human embryonic stem cell self-renewal via alphavbeta5 integrin, Stem Cells (2008), 28:2257-2265).

The extracellular domain of integrins can bind ECM proteins used in hESC support such as collagen, fibronectin, laminin and vitronectin as well as members of the SIBLING family (Small Integrin Binding Ligand, N-Linked Glycoproteins, e.g., osteopontin and bone sialoprotein). Integrin clustering occurs after ECM adhesion promoting lateral association with other cell surface receptors and increases in the cytoplasmic concentration of cell signaling molecules such as PI3-kinase and MEK-ERK, which are involved in hESC maintenance (see J. Li, et al., MEK/ERK signaling contributes to the maintenance of human embryonic stem cell self-renewal, Differentiation (2007), 75:299-307).

Recently, the Hubbell laboratory developed and tested various synthetic substrates for their capacity to maintain mouse ES cell self-renewal and concluded that simultaneous ligation of $\alpha 5 \beta 1$-, $\alpha v \beta 5$-, $\alpha 6 \beta 1$-, and $\alpha 9 \beta 1$ integrins promotes stemness of ES cells. These integrins have also been implicated in the regulation of mouse and human ES cell self-renewal in a number of other studies performed under various growth conditions (see Sandhanakrishnan Cattavarayan, et al., α6β1- and αv-integrins are required long-term self-renewal of murine embryonic stem cells in the absence of LIF, *BMC Cell Biology* (2015), 16:3; Y. Meng, et al. Characterization of integrin engagement during defined human embryonic stem cell culture, *FASEB J.* 2010, 24(4): 1056-65; S. R. Braam, et al., Recombinant vitronectin is a functionally defined substrate that supports human embryonic stem cell self-renewal via αvβ5 integrin. *Stem Cells.* 2008, 26(9):2257-65).

This disclosure also provides a microenvironmentally defined 3D surface that activates α5β1, α6β1 and/or αvβ5 simultaneously or sequentially in order to regulate signaling pathway for self-renewal and pluripotency maintenance of a stem cell. Any suitable substrate protein containing peptide ligand to activate integrin α5β1-, αvβ5-, α6β1, or α9β1 simultaneously or sequentially to support self-renewal and pluripotency of a stem cell. In one embodiment, the microenvironment surface provides a substrate protein presenting α5β1 integrin activating motif or heparin binding motif derived from fibronectin domain III. Any suitable α5β1 integrin activating- or heparin binding motif can be selected from RGD (SEQ ID NO:15), GRGDSP (SEQ ID NO:16), PHSRN-RGDSP (SEQ ID NO:17), SPPRRARVT (SEQ ID NO:18), WQPPRARI (SEQ ID NO:19), KNNQK-SEPLIGRKKT (SEQ ID NO:20), or its combination of α5β1 integrin-activating motif and heparin binding motif.

In another embodiment, the microenvironment surface provides a substrate protein presenting α6β1 integrin-activating motif-derived laminin a1 or laminin α5 LG domain to support self-renewal and pluripotency of a stem cell. Any suitable α6β1 integrin-activating motif can be selected from GKNTGDHFVLYM (SEQ ID NO:22), VVSLYN-FEQTFML (SEQ ID NO:23), RFDQELRLVSYN (SEQ ID NO:24), RLVSYSGVLFFLK (SEQ ID NO:25), ASKAIQV-FLLGG (SEQ ID NO:26), VLVRVERATVFS (SEQ ID NO:27), TVFSVDQDNMLE (SEQ ID NO:28), RLRG-PQRVFDLH (SEQ ID NO:29), FDLHQNMGSVN (SEQ ID NO:30), QQNLGSVNVSTG (SEQ ID NO:31), SRATAQK-VSRRS (SEQ ID NO:32), TWYKIAFQRNRK (SEQ ID NO:45), NRWHSIYITRFG (SEQ ID NO:46).

In another embodiment, the microenvironment surface provides a substrate protein presenting cadherin-derived peptide motif to support self-renewal and pluripotency of a stem cell. Any suitable cadherin binding motif can be selected from SHAVSS (SEQ ID NO:48), LFSHAVSSNG (SEQ ID NO:49), ADTPPV (SEQ ID NO:50), DQNDN (SEQ ID NO:51), HAVDI (SEQ ID NO:52), LRA-HAVDING (SEQ ID NO:53).

In another embodiment, the 3D microenvironment surface provides a substrate protein presenting a combinatorial motif of α5β1 integrin-activating motif and α6β1 binding motif at the same time to support self-renewal and pluripotency of a stem cell. Suitable combinatorial motif is a combination of PHSRN-RGDSP (SEQ ID NO:17) and NRWHSIYITRFG (SEQ ID NO:46) to support self-renewal and pluripotency of a stem cell.

Fibroblast growth factors (FGFs) are essential for maintaining self-renewal in human embryonic stem cells and induced pluripotent stem cells. Recombinant basic FGF (bFGF or FGF2) is conventionally used to culture pluripotent stem cells. Today, FGF family consists of 23 members including acidic and basic fibroblast growth factor, and each FGF has canofin, hexafin, and decafin domain (S. Li, et al., Fibroblast growth factor-derived peptides: functional agonists of the fibroblast growth factor receptor, *J. Neurochem.* 2008 February, 104(3):667-82; S. Li, et al., Agonists of fibroblast growth factor receptor induce neurite outgrowth and survival of cerebellar granule neurons, *Dev. Neurobiol.* 2009, 69(13):837-54; Shizhong Li, et al., Neuritogenic and Neuroprotective Properties of Peptide Agonists of the Fibroblast Growth Factor Receptor, *Int. J. Mol. Sci.* 2010, 11(6): 2291-2305).

FGFRs are transmembrane glycoproteins with three extracellular domains, Ig1, Ig2 and Ig3. An FGFR fragment Ig2 and Ig3 is the minimal unit sufficient for specific ligand binding (see V. Manfé, et al., Peptides derived from specific interaction sites of the FGF 2-FGF receptor complexes induce receptor activation and signaling (see *J. Neurochem.* 2010, 114(1):74-86; S. K. Olsen, et al. (2004), Insights into the molecular basis for fibroblast growth factor receptor autoinhibition and ligand binding promiscuity, *Proc. Natl Acad. Sci. USA* 101:935-940).

Bell et al. (see 2000 Rotational coupling of the transmembrane and kinase domains of the Neu receptor tyrosine kinase, *Mol. Biol. Cell* 11:3589-3599) demonstrated that activation of receptor tyrosine kinases requires specific orientations of the kinase domains in a formed receptor dimer. The ligand binding mediates the optimal rotational positioning of the individual monomers within the dimer and thus the specific orientation of the catalytic domains. Binding of different agonists, such as FGF2 and canofins, resulted in different modes of orientation of catalytic domains yielding differences in receptor activation (see V. Manfe, et al., Peptides derived from specific interaction sites of the fibroblast growth factor 2-FGF receptor complexes induce receptor activation and signaling, *J. Neurochem.* 2010, 114(1): 74-86).

When a growth factor binds to the extracellular domain of a receptor tyrosine kinase (RTK), its dimerization is triggered with other adjacent RTKs. Dimerization leads to a rapid activation of the protein's cytoplasmic kinase domains and the activated receptor as a result then becomes autophosphorylated on multiple specific intracellular tyrosine residues, resulting in signal transduction cascade.

Recent studies have demonstrated that the immobilization of soluble factors such as FGF, TGF or cytokines to the ECM plays an important role in mediating their biological effects (see C. C. Rider (2006), Heparin/heparan sulphate binding in the TGF-beta cytokine superfamily, *Biochem. Soc. Trans.* 34:458-460). Presentation of soluble factors in an immobilized fashion alters their local effective concentration, bioavailability, and stability, and thereby modulates their effects on target cells. For example, NSC-proliferative regions in the SVZ are situated in proximity to regions, in which growth factors, including basic fibroblast growth factor-2, are concentrated by heparan sulfate proteoglycan (HSPG) (see F. Mercier et al. (2002), Anatomy of the brain neurogenic zones revisited: fractones and the fibroblast/macrophage network, *J. Comp. Neurol.* 451:170-188).

This disclosure provides the FGF mimetic comprises recombinant mussel adhesive protein functionalized with FGF-derived peptide motif derived from hexafin domain or canofin domain. Preferably, FGF mimetic peptide motif can be selected from hexafin domain-derived ANRYLAM-KEDGRLLAS (SEQ ID NO:33) or canofin domain-derived HFKDPKRLYCK (SEQ ID NO:34), FLPMSAKS (SEQ ID NO:35), KTGPGQKAIL (SEQ ID NO:76).

In one embodiment of this disclosure, a 3D microenvironment surface that combinatorially regulates the activity of both integrin and growth factor receptor to support self-renewal and pluripotency of murine embryonic stem cell is provided. The microenvironment surface comprises a substrate protein functionalized with a peptide such as fibronectin-derived peptide PHSRN-GRGDSP (SEQ ID NO:17) to target α5β1 and FGF2-derived peptide ANRYLAMKEDGRLLAS (SEQ ID NO:33) to target FGF receptor; FGFR2IIIc.

This disclosure also provides a 3D microenvironment surface to activate TGF receptor or Frizzle receptor to induce signaling pathway to activate transcriptional factors for self-renewal and pluripotency of pluripotent stem cell. A recombinant mussel adhesive protein as a substrate protein containing TGF mimetic peptide to bind to TGFβ receptor domain TβRI or TβRII can be used in this disclosure. Preferably, TGFβ mimetic peptide can be selected from LTGKNFPMFHRN (SEQ ID NO:37), MHRMPSFLPTTL (SEQ ID NO:38).

In one embodiment of this disclosure, a 3D microenvironment surface that combinatorially regulates the activity of both integrin and growth factor receptor to support self-renewal and pluripotency of an embryonic stem cell is provided. The microenvironment surface comprises a substrate protein presenting a combinatorial motif to activate α5β1 integrin and TGFβ receptor at the same time. The combinatorial motif is a combination of the substrate protein functionalized with a peptide such as fibronectin-derived peptide PHSRN-GRGDSP (SEQ ID NO:17) to target α5β1 and TGFβ-derived peptide LTGKNFPMFHRN (SEQ ID NO:37), or MHRMPSFLPTTL (SEQ ID NO:38).

This disclosure provides a 3D microenvironment surface that generates WNT/β-catenin signaling pathway by presenting WNT 1 peptide motif LCCGRGHRTRTQRVTERCNC (SEQ ID NO:39) or LGTQGRLCNKTSEGMDGCEL (SEQ ID NO:40). In one embodiment of this disclosure, a microenvironment surface that combinatorially regulates the activity of both integrin and frizzled receptor to support self-renewal and pluripotency of an embryonic stem cell is provided. The microenvironment surface comprises a substrate protein presenting a combinatorial motif to activate α5β1 integrin and frizzled receptor at the same time. The combinatorial motif is a combination of the substrate protein functionalized with a peptide such as fibronectin-derived peptide PHSRN-GRGDSP (SEQ ID NO:17) to target α5β1 and WNT-derived peptide LCCGRGHRTRTQRVTERCNC (SEQ ID NO:39) or LGTQGRLCNKTSEGMDGCEL (SEQ ID NO:40).

This disclosure provides a 3D microenvironment surface that generates LIF/STAT3 signaling pathway by presenting LIF peptide motif IVPLLLLVLH (SEQ ID NO:41) or YTAQGEPFPNNVEKLCAP (SEQ ID NO:42).

Various studies suggest that co-clustering or synergism occurs between downstream signaling molecules, once the basic requirements are met: growth factor receptor ligand binding, integrin occupancy by a ligand and clustering of each type of receptor (see M. A. Schwartz and V. Baron, Interactions between mitogenic stimuli or a thousand and one connections, Curr. Opin. Cell Biol. 11:197-202 (1999); K. M. Yamada and E. H. J. Danen, Integrin signaling, in Signaling Networks and Cell Cycle Control (ed. J. S. Gutkind) 1-25 (Humana Press, Totowa, N.J., 2000); S. Miyamoto, et al., Integrins can collaborate with growth factors for phosphorylation of receptor tyrosine kinases and MAP kinase activation: roles of integrin aggregation and occupancy of receptors, J. Cell Biol. 135:1633-1642 (1996)).

This disclosure provides a 3D microenvironment surface to activate at least two different receptors simultaneously by presenting a substrate protein having combinatorial motifs comprising at least two different peptide motifs that bind to at least two different receptors, respectively. The suitable combinatorial motifs may include one or more spacers between two peptide motifs to optimize flexibility and/or solubility and so afford increased affinity and/or bioavailability. The combinatorial motifs may have a peptide spacer sequence of at least two amino acids, preferably 2-15 amino acids, appended to the C-termini of at least one of the two peptide motifs.

In one embodiment of this disclosure, a 3D microenvironment surface that combinatorially regulates the activity of both integrin and growth factor receptor to support self-renewal and pluripotency of murine embryonic stem cell is provided. The microenvironment surface comprises mussel adhesive protein as a substrate protein, functionalized with two peptide motifs; one is fibronectin-derived peptide PHSRN-GRGDSP (SEQ ID NO:16) to target α5β1 and the other is FGF2-derived peptide ANRYLAMKEDGRLLAS (SEQ ID NO:33) to target FGF receptor; FGFR2IIIc.

In one embodiment of this disclosure, a combinatorial 3D microenvironment surface comprising a nanofiber substrate having an average diameter of 100 nm to 20 microns, wherein the nanofiber surface presents extracellular components comprising extracellular matrix mimetic, growth factor mimetic, WNT mimetic, cytokine mimetic such as IL-3, LIF mimetic or combinations thereof.

The disclosure provides for a device of extracellular microenvironment array comprising:

(a) obtaining an electroprocessable biofunctional composition;

(b) placing the composition on a solid support in a pattern; and (c) electroprocessing the composition to obtain the extracellular microenvironment array.

The following examples are provided to demonstrate preferred embodiments of this disclosure and the disclosure is not intended to be limited in scope by the specific embodiments described herein, which are intended for the purposes of exemplification only. Functionally equivalent products, compositions and methods are clearly within the scope of the disclosure, as described herein.

EXAMPLES

Example 1. Preparation of Electrospinnable Composition that Provides an Extracellular Microenvironment PVDF with an average molecular weight of 400 kDa (Solvay Plastics, Paris), PAN with an average molecular weight of 150 kDa (Sigma-Aldrich, St. Louis) were dissolved in DMAc, respectively, to prepare 20 wt % solution. Each polymer solution was mixed together and the mixture ratio was summarized in Table 2.

The electrospinnable solution was placed in a plastic syringe fitted with a 27 G needle. A syringe pump (KD Scientific, USA) was used to feed the polymer solution into the needle tip. A high voltage power supply (NanoNC Co. Ltd.) was used to charge the needle tip. The nanofibers were collected onto grounded aluminum foil target located at a certain distance from the needle tip. The fiber meshes were then removed, placed in a vacuum chamber for two days to remove residual solvent, and then stored in a desiccator.

TABLE 2

| Electrospinnable solution composition | |
|---|---|
| Structural Polymer | Solvent |
| PVDF/PAN = 100/00 | DMAc 5 mL |
| PVDF/PAN = 70/30 | DMAc 5 mL |
| PVDF/PAN = 50/50 | DMAc 5 mL |
| PVDF/PAN = 30/70 | DMAc 5 mL |
| PVDF/PAN = 0/100 | DMAc 5 mL |

Example 2. Characterization of an Extracellular Microenvironment

Figure 2A:
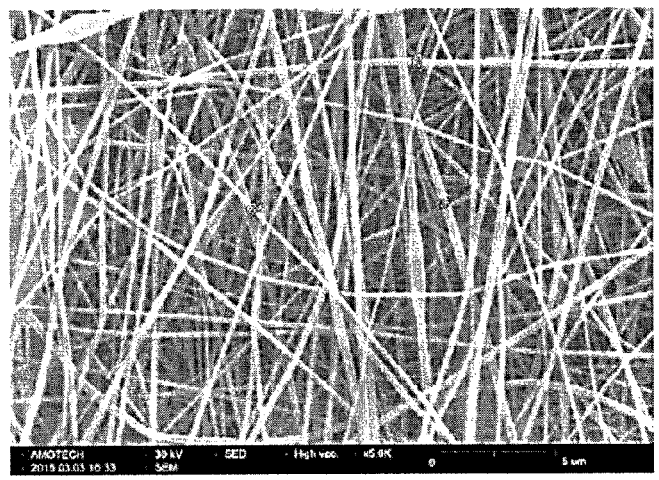
FIGS. 2A-2C represent scanning electron micrographs of nanofiber microenvironment having the same diameter size (400 nm) but having different surfaces. The hydrophobicity: 2A>2B>2C.
Figure 2B:
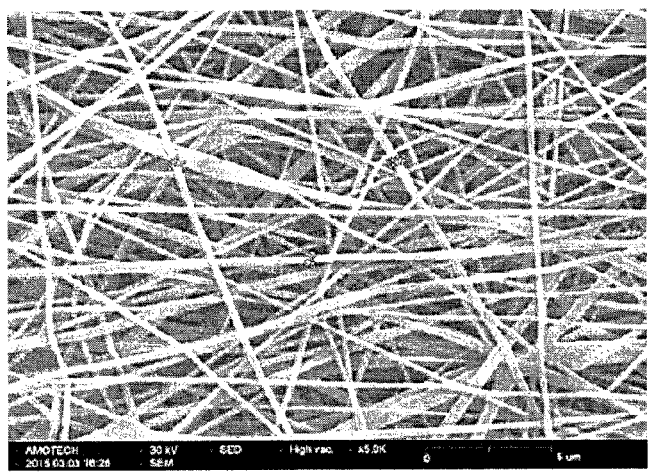
Figure 2C:
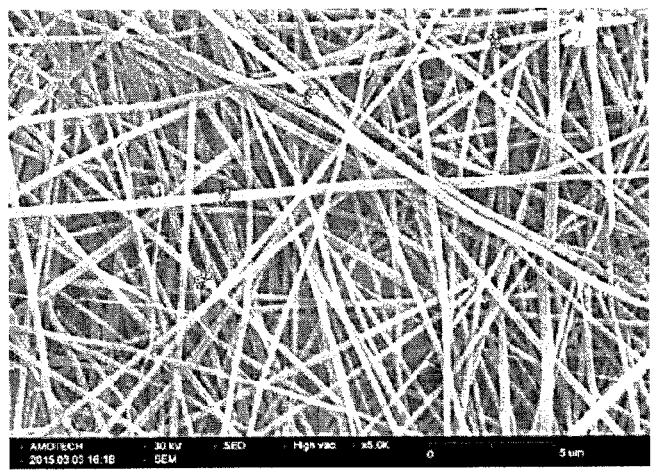

The nanofiber membranes obtained were observed using a scanning electron microscope. The average diameter indicated is an average of at least three independent measurements, and the average diameter is 400 nm for all samples. The images corresponding to these fibrous microenvironments, obtained by scanning electron microscopy, are shown in FIG. 2A for PVDF/PAN (70/30), FIG. 2B for PVDF/PAN (50/50), and FIG. 2C for PVDF/PAN (30/70).

Example 3. Self-Renewal of Murine Embryonic Stem Cell

The ability of the microenvironment to support self-renewal of mESCs was evaluated by serial passaging of mESCs on the electroprocessed extracellular microenvironment as prepared in EXAMPLE 1.

For the maintenance of murine embryonic stem cell cultured on poly-D-lysine-coated surface (PDL, Sigma-Aldrich), DMEM Glutamax (GIBCO, Life Technology) containing high glucose 4.5 g/L, Na-pyruvate (0.11 g/L) and L-glutamine was used with L-Glutamine (Invitrogen), 1% non-essential amino acid (Sigma-Aldrich), 50 U/mL Penicillin/streptomycin (GIBCO) and 0.1 mM 2-Mercaptoethanol (GIBCO) as the basal medium, which was added with 20% fetal bovine serum (FBS, Hyclone) and leukemia inhibitory factor (LIF, 1,000 units/mL, Chemicon) at 37° C., 5% CO2 incubator.

Figure 3:
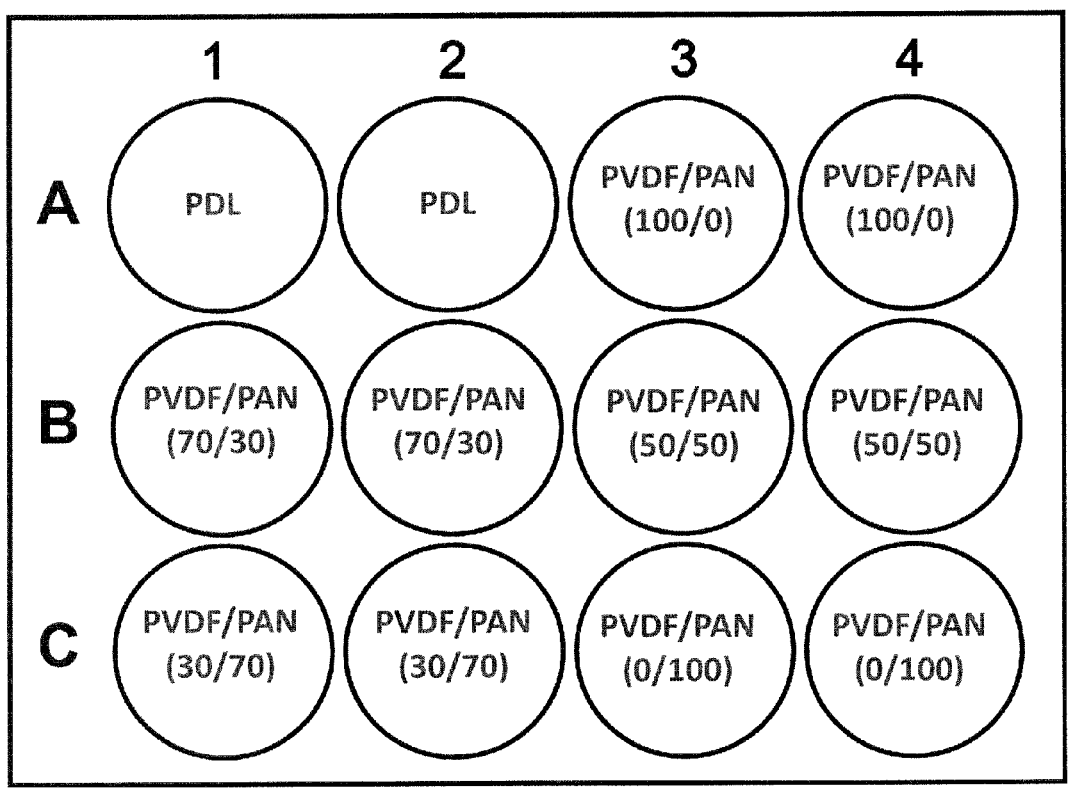
FIG. 3 shows the layout of microenvironment array.

To elucidate the effect of fibrous microenvironment on self-renewal of murine embryonic stem cells, the cells ($6\times10^4$) were cultured for 48 hours on six different microenvironments placed in 12-well plates as schematically represented in FIG. 3.

Example 4. Alkaline Phosphatase Staining Assay

Figure 4A:
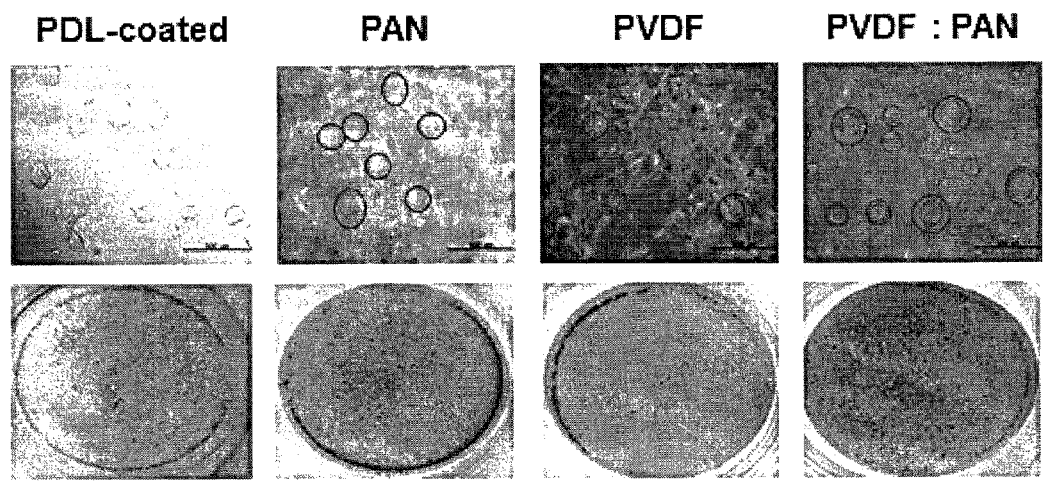
FIGS. 4A and 4B show embryonic stem cell cultured on nanofiber microenvironment stained with alkaline phosphatase.
Figure 4B:
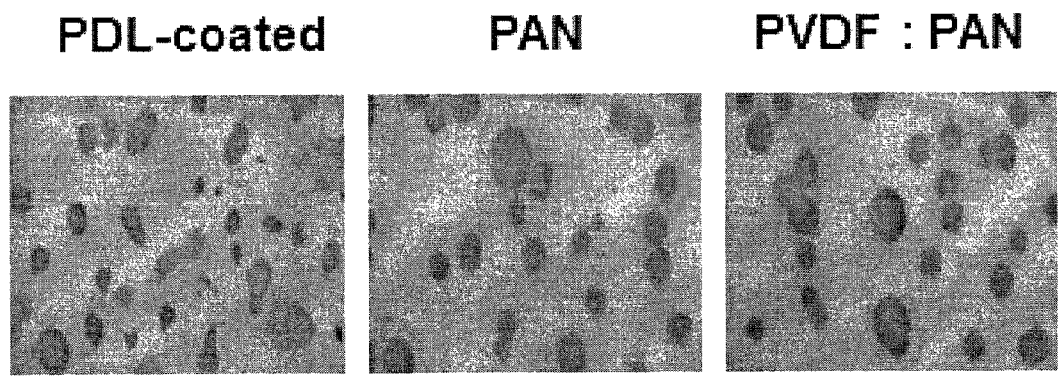

Cells were washed in PBS and fixed in formaldehyde (37%) for 30 seconds, washed and stained for 15 minutes in 100 µL of FBB Alkaline solution (Sigma-Aldrich) in sodium nitrile solution. Stained cells were analyzed on an Olympus microscope. FIGS. 4A and 4B show the murine stem cell cultured on PVDF/PAN nanofiber membrane indicated self-renewal without loss of its differential potential while the stem cells cultured on PDL-coated surface indicated the differentiated state.

Example 5. Immunocytochemistry

Several biomarkers indicating undifferentiated ESCs and iPS cells were examined using immunofluorescent staining. Cells were fixed using 4% paraformaldehyde (Sigma-Aldrich) in 0.5% TRITON® X-100 solution at room temperature for 25 minutes, and washed three times with PBS for 5 minutes each time, and added with 10% normal goat serum (Sigma-Aldrich) at room temperature for 30 minutes.

As the primary antibody, monoclonal antibodies against SSEA1 (Santa Cruz Biotechnology) diluted at a concentration of 1:1,000 and Oct4 (Santa Cruz Biotechnology) diluted at a concentration of 1:1,000 was added to the above solution. The antibody was reacted for 24 hours at 4° C. and washed with PBS three times with 0.5% TRITON® X-100 added PBS. As the secondary antibody, goat anti-mouse ALEXA FLUOR® 546 (Invitrogen) was diluted with 0.5% TRITON® X-100 added PBS diluted at a concentration of 1:1,000, and reacted for 1.5 hours. Thereafter, the cells were reacted with 10 µg/mL of TO-PRO3 (Invitrogen) for the cell nucleus staining, and observed with laser scanning microscopy (Zeiss).

Figure 5:
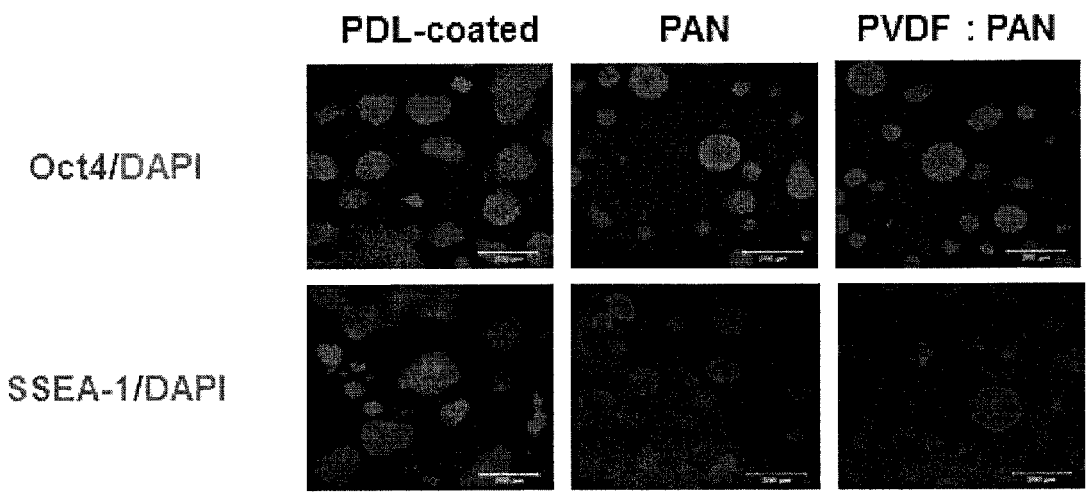
FIG. 5 shows Oct4 staining of embryonic stem cell cultured on nanofibrous microenvironment.

As shown in FIG. 5, all cells cultured on nanofiber membrane expressed Oct4 and SSEA1, the key biomarkers of murine stem cells.

Example 6. PCR Analysis for Gene Expression Profile

The cells cultured on each microenvironment were collected and RNA preparation and cDNA synthesis were accomplished. RT-PCR reaction was conducted with this cDNA as template using the primers for amplification of each marker gene fragment.

Figure 6:
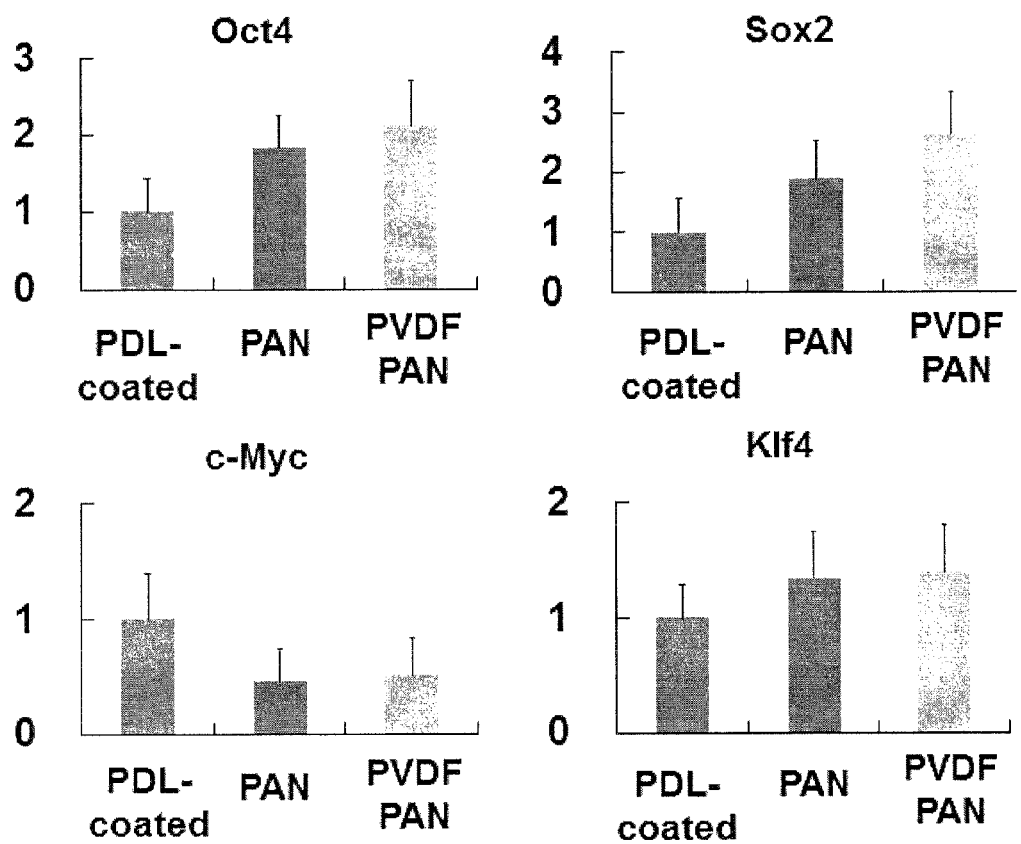
FIG. 6 shows the RT-PCR analyses of pluripotency markers OCT4, SOX2, MYC and KLF4 from stem cells cultured on different microenvironment.

As shown in FIG. 6 by quantitative RT-PCR analyses of OCT4, SOX2, MYC, and KLF4 expression, the nanofibrous environment supported the self-renewal of mouse embryonic stem cell.

Figure 7:
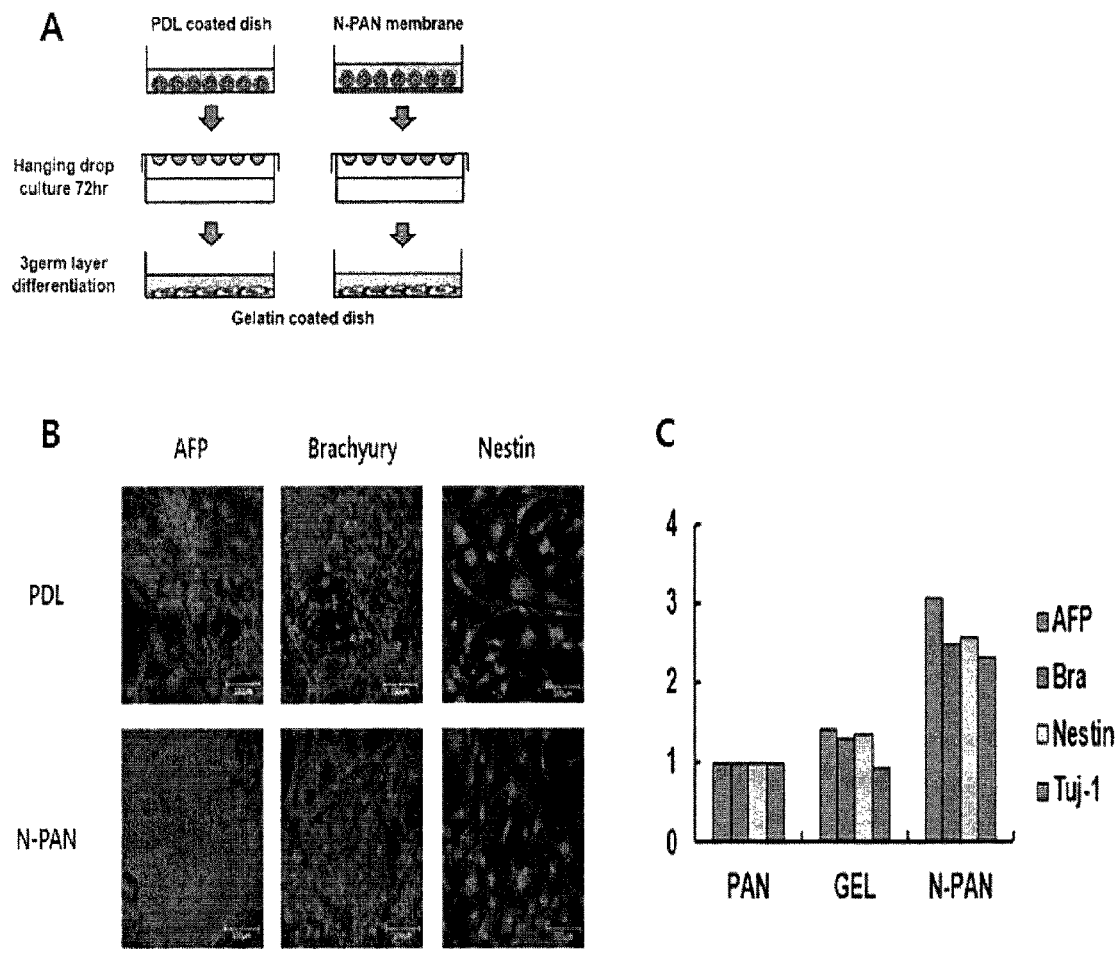
FIG. 7 represents characterization of pluripotency of human-induced pluripotent stem cell cultured on nanofibrous matrix.

Example 7. Evaluation of Differentiation Potential of Murine ESC Cultured on Nanofiber Matrix Embryoid body (EB) formation from ES cells is a common method for producing different cell lineages and hanging drop culture is a widely used EB formation induction method. Using handing drop culture, embryoid body (EB) that were formed from the murine embryonic stem cells cultured on the N-PAN-based nanofiber matrix, subsequently differentiated into three germ layers, characterized by immunostaining and qPCR as shown in FIG. 7.

Figure 8A:
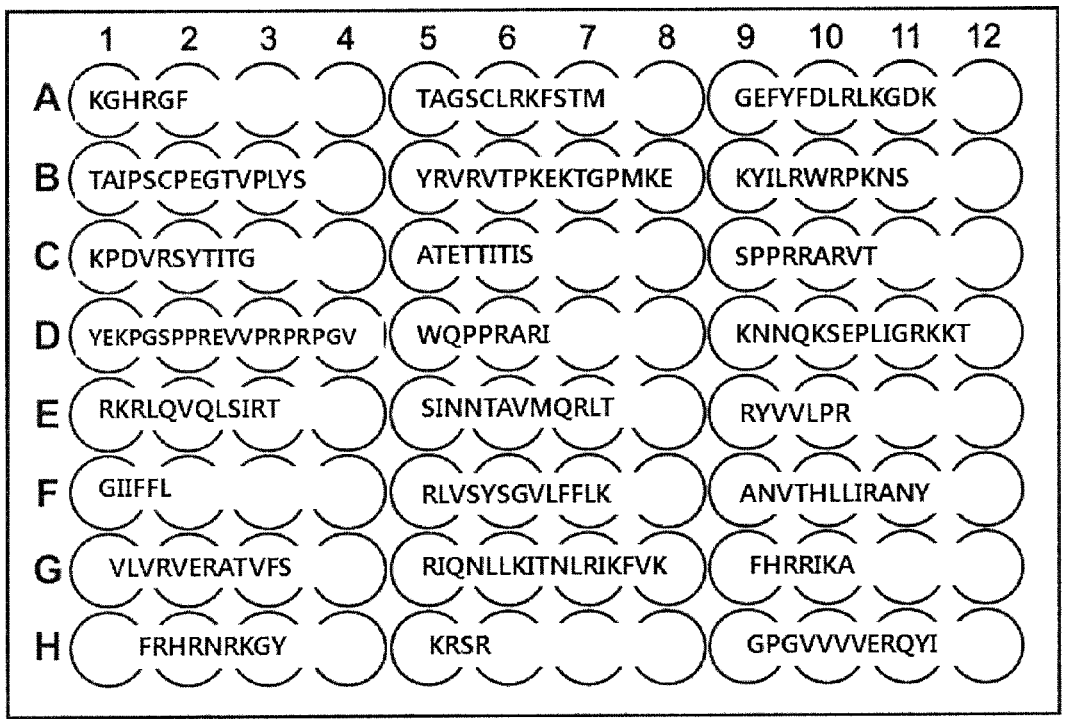
FIGS. 8A and 8B represent layout of microenvironment array to screen optimal extracellular microenvironment to support self-renewal and proliferation of embryonic stem cell.
Figure 8B:
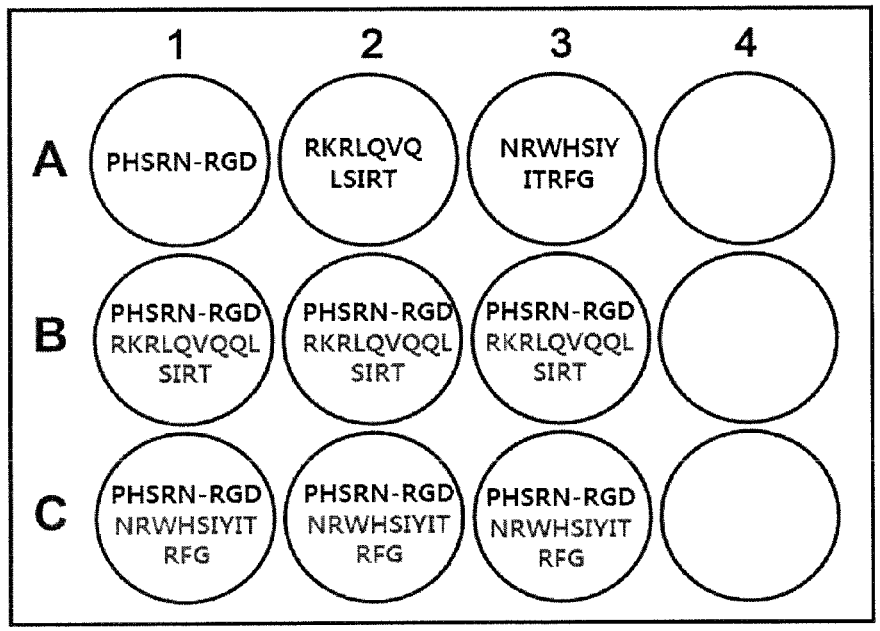

Example 8. Screening Biochemical Factors to Support Self-Renewal and Proliferation of Embryonic Stem Cell To identify optimal biochemical cues for self-renewal of murine embryonic stem cells, a screening for mESC adhesion and growth was performed. Briefly, 96 different ECM mimetics from fibronectin, laminin, vitronectin, cadherin. WNT, and LIF, at optimized concentration, were coated on a 12-microwell plate. FIGS. 8A and 8B showed some of coated plates, single peptide motif-coated microwell plate in FIG. 8A and combination of two different peptide motifs-coated plates in FIG. 8B. Then, $6\times10^4$ cells were added to each microwell and incubated in a humidified cell culture incubator with controlled atmosphere (37° C., 10% $CO_2$).

FIG. 8A also includes the following sequences: KGHRGF (SEQ ID NO:54), TAGSCLRKFSTM (SEQ ID NO:55), GEFYFDLRLKGDK (SEQ ID NO:56), TAIPSCPEGTVPLYS (SEQ ID NO:57), YRVRVTPKEKTGPMKE (SEQ ID NO:58), KYILRWRPKNS (SEQ ID NO:59), KPDVRSYTITG (SEQ ID NO:60), ATETTITIS (SEQ ID NO:61), SPPRRARVT (SEQ ID NO:18), YEKPGSPPREVVPRPRPGV (SEQ ID NO:62), WQPPRARI (SEQ ID NO:19), KNNQKSEPLIGRKKT (SEQ ID NO:20), RKRLQVQLSIRT (SEQ ID NO:21), SINNTAVMQRLT (SEQ ID NO:63), RYVVLPR (SEQ ID NO:64), GIIFFL (SEQ ID NO:65), RLVSYSGVLFFLK (SEQ ID NO:25), ANVTHLLIRANY (SEQ ID NO:66), VLVRVERATVFS (SEQ ID NO:67), RIQNLLKITNLRIKFVK (SEQ ID NO:68), FHRRIKA (SEQ ID NO:69), FRHRNRKGY (SEQ ID NO:70), KRSR (SEQ ID NO:71), and GPGVVVVERQYI (SEQ ID NO: 72).

FIG. 8B also includes the following sequences: PHSRN-RGD (SEQ ID NO:73), RKRLQVQLSIRT (SEQ ID NO:21), and NRWHSIYITRFG (SEQ ID NO:46).

Figure 9A:
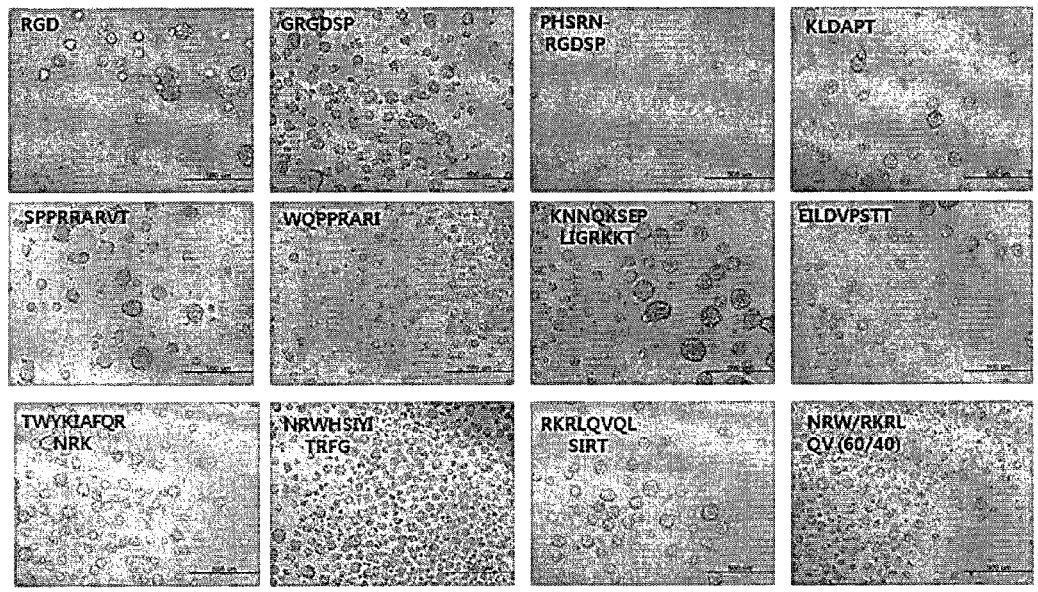
FIGS. 9A-9E represent the effect of integrin binding peptide motif, alone or in combination, on self-renewal and proliferation of embryonic stem cell.
Figure 9B:
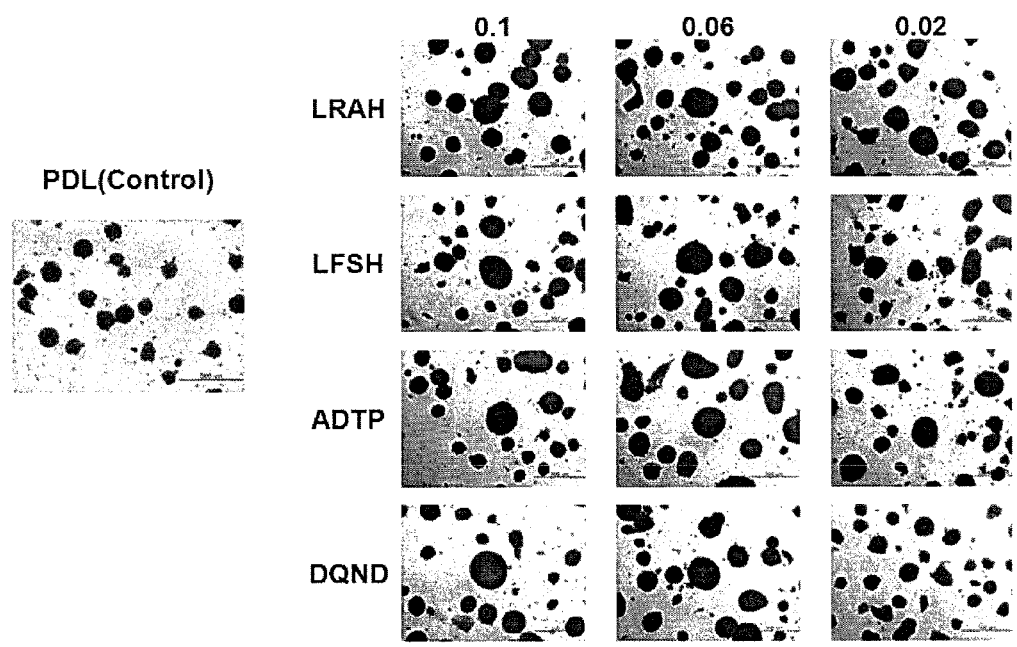

Example 9. Identification of Biochemical Factors to Support Self-Renewal and Proliferation of Embryonic Stem Cell After 96 hours, all cells were stained with AP as described in Example 4 Alkaline phosphatase staining assay. As shown in FIGS. 9A and 9B, the surface presenting integrin α5β1 binding motif such as RGD (SEQ ID NO:15) and PHSRN-RGDSP (SEQ ID NO:17) or α6β1 binding motif such as NRWHSIYITRFG (SEQ ID NO:46) provided more favorable environment to support self-renewal of murine embryonic stem cell than the surface presenting α4β1 binding motif such as REDV (SEQ ID NO:47).

Figure 9C:
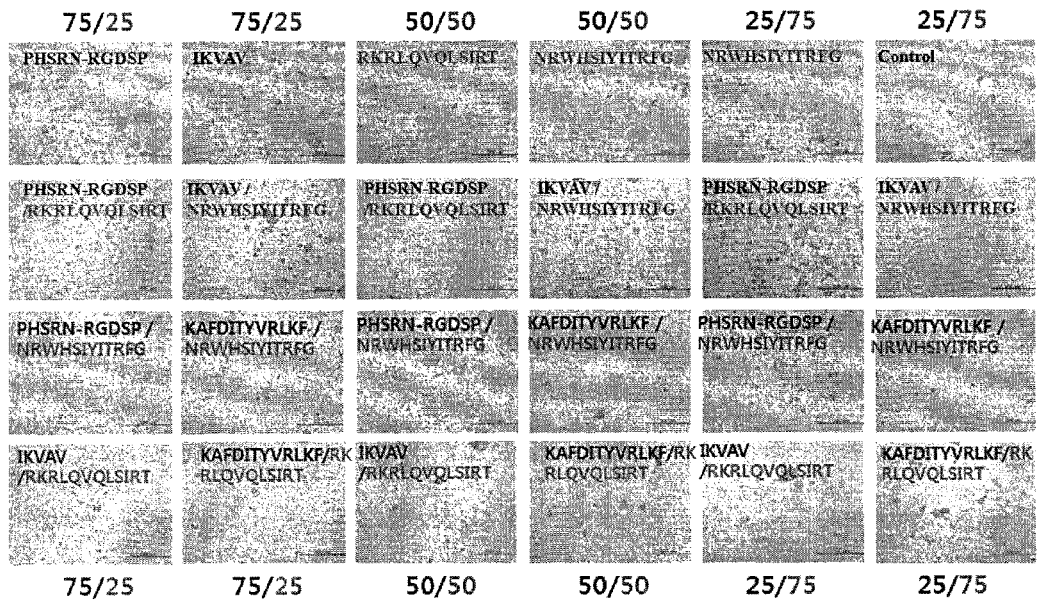

The presentation of combinatorial peptide motifs, for example, PHSRN-RGDSP/NRWHSIYITRFG (SEQ ID NO:46) (50/50) induced synergistic effect on self-renewal of murine embryonic stem cell by making the colony spherical as seen in FIG. 9C, while the combinatorial presentation of α5β1/syndecan binding motif (PHSRN-RGDSP/RKRLQVQLSIRT (SEQ ID NO:17/SEQ ID NO:21)) did not show any synergistic effect on the self-renewal.

Cadherin-derived motif presenting surface also supports self-renewal of murine embryonic stem cell as shown in FIG. 9B. AP assay revealed all cadherin-derived peptide motif supported self-renewal.

Figure 10A:
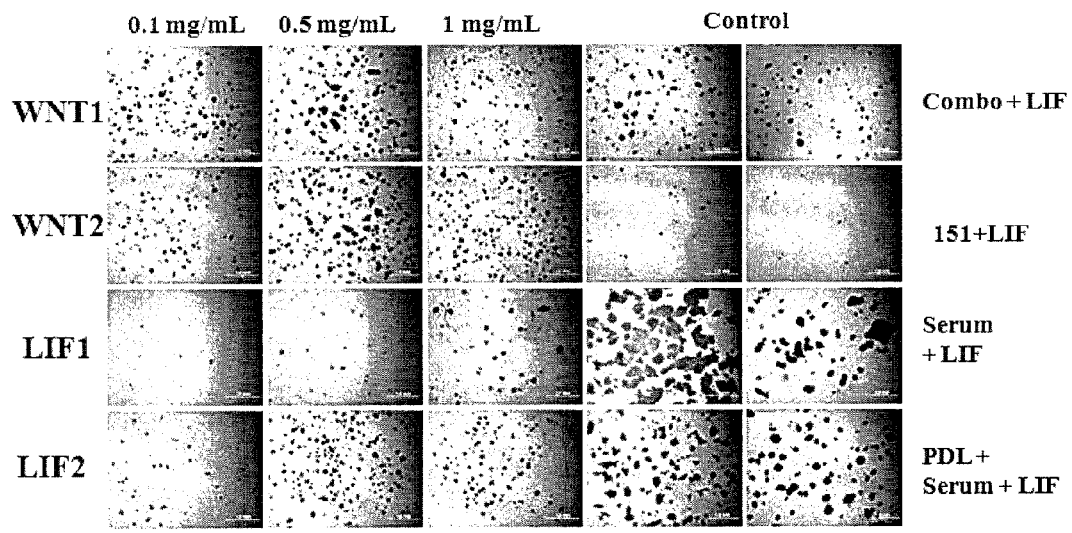
FIGS. 10A-10C represent the inhibitory effect of WNT and LIF-derived peptide motif on stem cell differentiation.
Figure 10B:
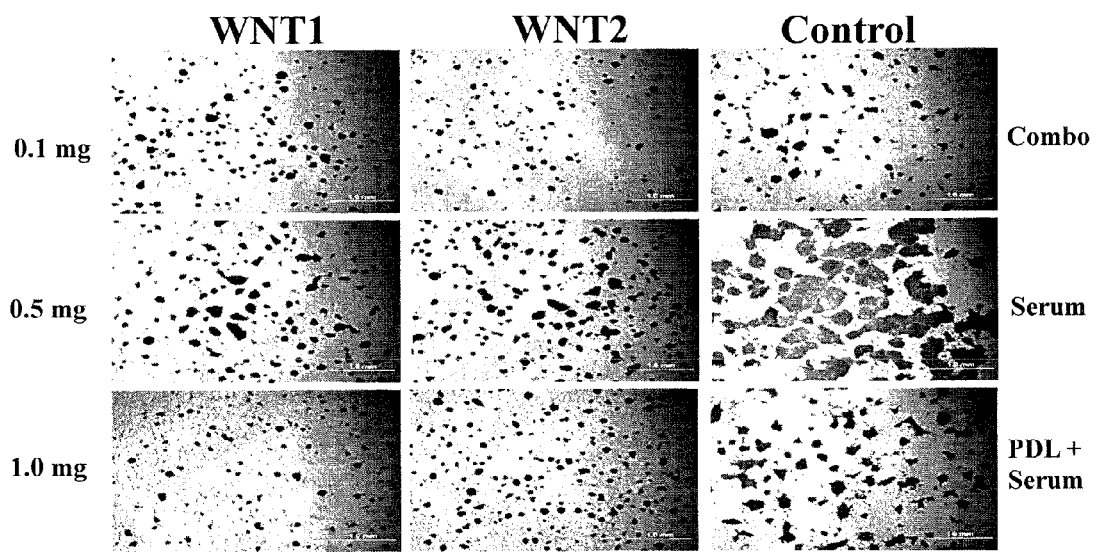
Figure 10C:
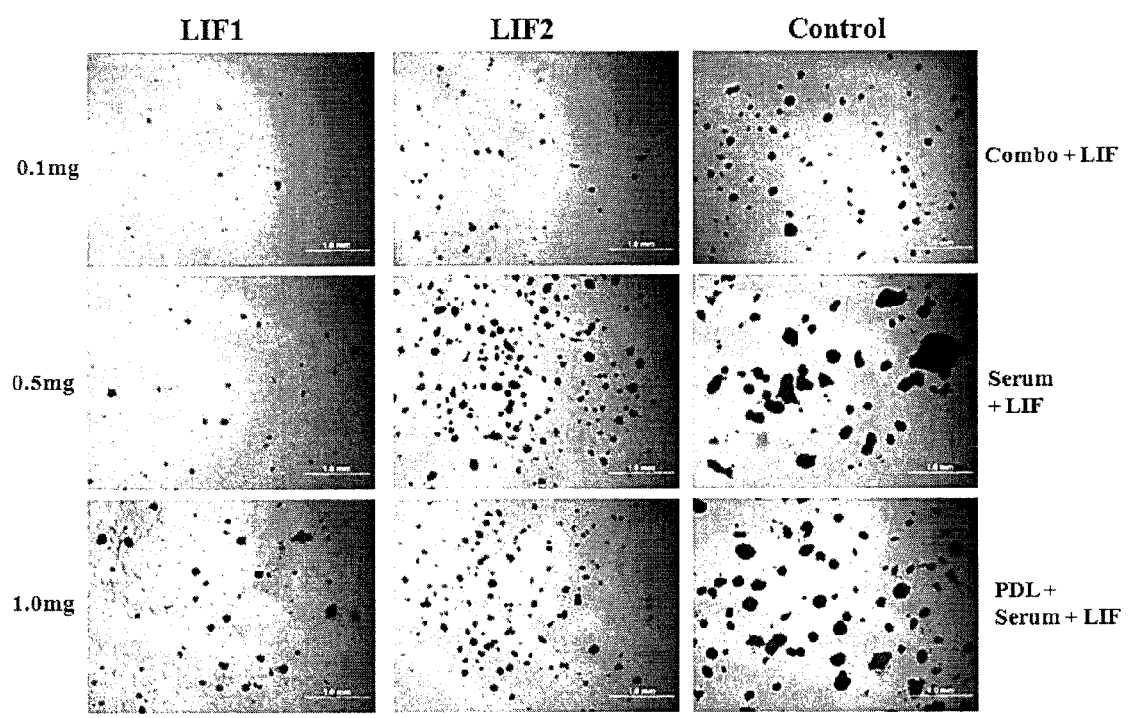

LIF and WNT-derived peptide motif also support stemness maintenance of murine embryonic stem cell by inhibiting the differentiation depending on the concentration of these peptide motifs on the surface as seen in FIGS. 10A-10C. FIG. 10B shows the effect of two WNT-derived peptide motifs on self-renewal and proliferation in serum-free conditions, similar to that of PHSRN-RGDSP (SEQ ID NO:17) motif. While WNT-derived peptide motif seems to positively influence differentiation inhibition as well as proliferation, the effect of LIF-derived peptide motif seems to be limited only to differentiation inhibition. The colony size of murine stem cells is much smaller than that of murine stem cells culture on WNT-derived peptide presenting surface.

FIG. 9A also includes: GRGDSP (SEQ ID NO:16), PHSRN-RGDSP (SEQ ID NO:17), KLDAPT (SEQ ID NO:43), SPPRRARVT (SEQ ID NO:18), WQPPRARI (SEQ ID NO:19), KNNQKSEPLIGRKKT (SEQ ID NO:20), EILDVPSTT (SEQ ID NO:44), TWYKIAFQRNRK (SEQ ID NO:45), NRWHSIYITRFG (SEQ ID NO:46), RKRLQVQLSIRT (SEQ ID NO:21), and RKRLQV (SEQ ID NO:74).

FIG. 9C also includes: PHSRN-RGDSP (SEQ ID NO:17), IKVAV (SEQ ID NO:77), RKRLQVQLSIRT (SEQ ID NO:21), NRWHSIYITRFG (SEQ ID NO:46), KAFDITYVRLKF (SEQ ID NO:75), and IKFAV (SEQ ID NO:78).

Figure 9D:
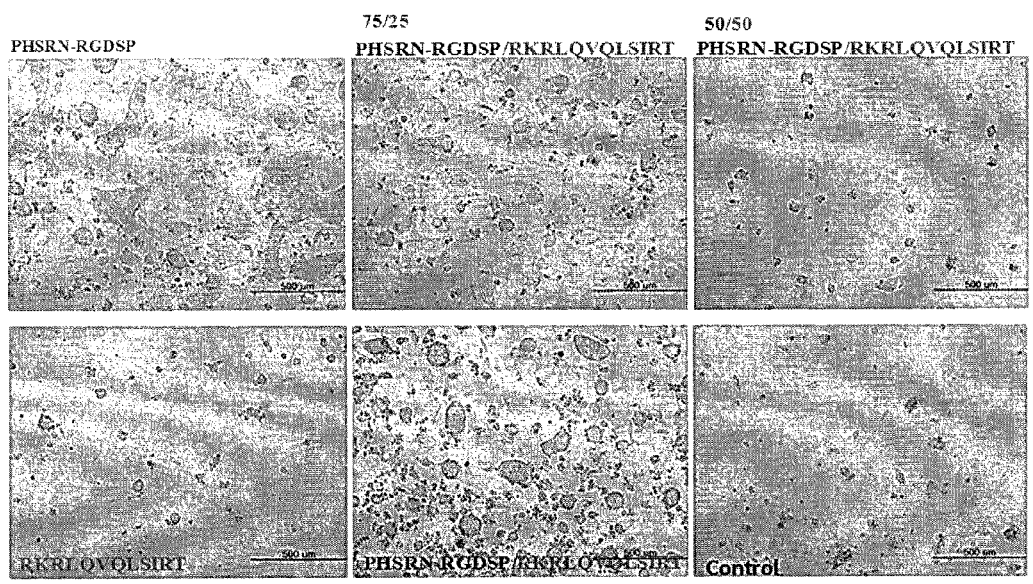

FIG. 9D also includes: PHSRN-RGDSP (SEQ ID NO:17) and RKRLQVQLSIRT (SEQ ID NO:21).

Figure 9E:
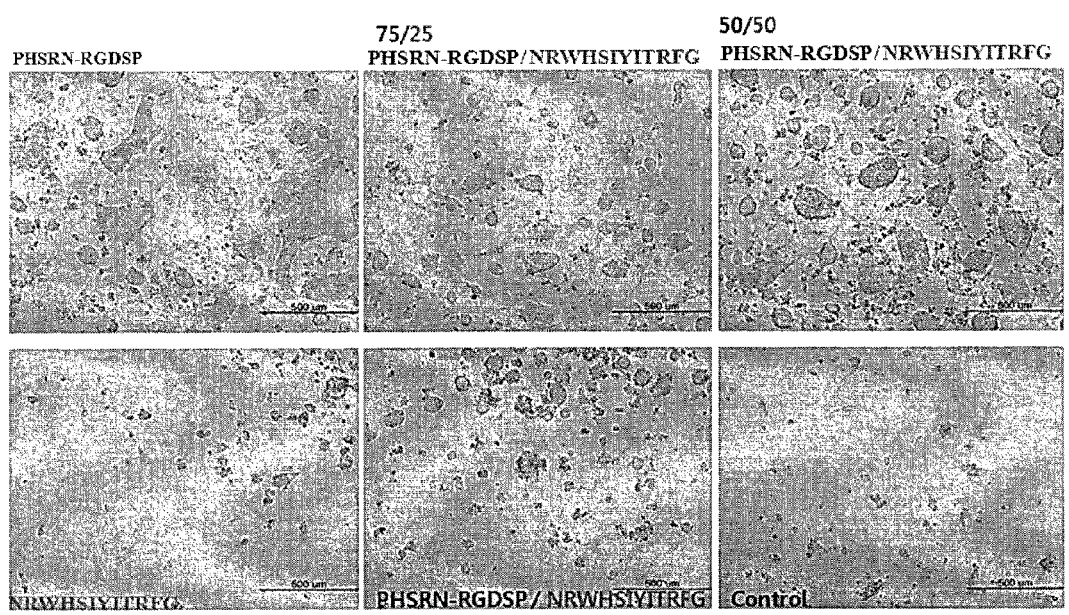

FIG. 9E also includes: PHSRN-RGDSP (SEQ ID NO:17), and NRWHSIYITRFG (SEQ ID NO:46).

Example 10. Effect of Biochemically and Physically Defined Nanofibrous Matrix on Murine Embryonic Stem Cell RGD (SEQ ID NO:15) and PHSRN-RGDSP (SEQ ID NO:17), activating integrin α5β1 to support self-renewal, were selected to investigate the effect of biochemical and physical cues on the self-renewal of murine embryonic stem cell.

Electrospinnable composition was prepared to make nanofiber of 200 nm diameter whose surface presenting RGD and PHSRN-RGDSP (SEQ ID NO:17) motif with the same procedure set forth in Example 1. N-PAN and PVDF-based nanofiber with these peptide motifs was used as a control. As a positive control, poly-d-lysine and gelatin-coated surface in serum conditions were used for comparison with N-PAN and PVDF nanofiber in serum-free conditions.

Figure 11:
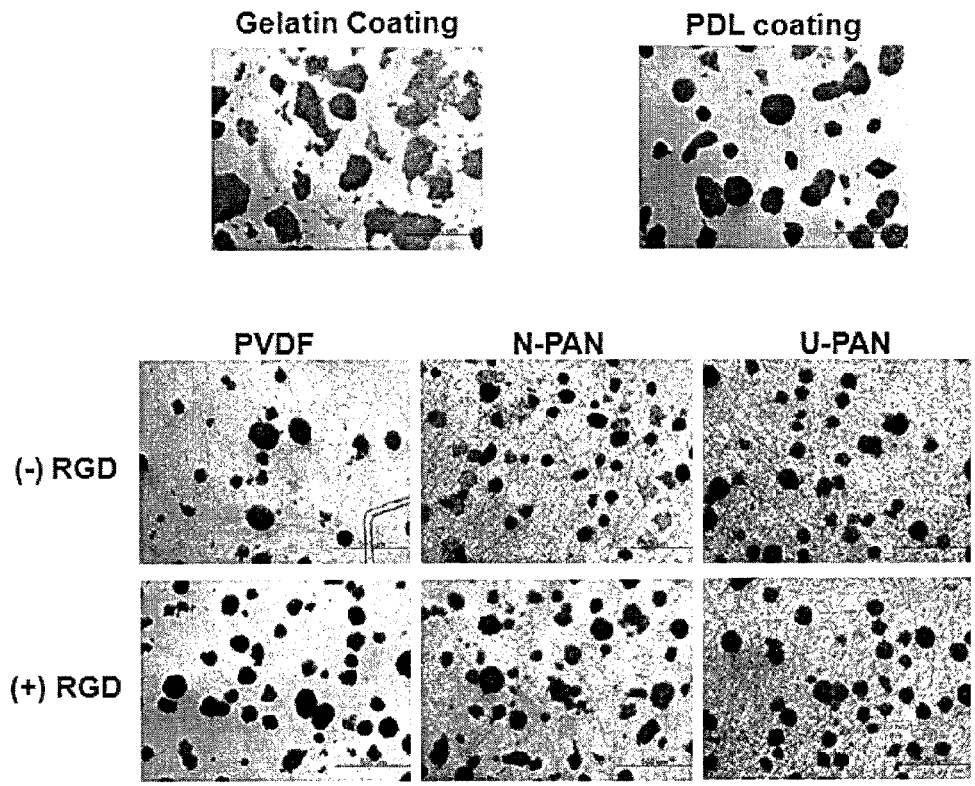
FIG. 11 represents the effect of biochemically and physically defined nanofibrous microenvironment on self-renewal of murine embryonic stem cell.

As seen in FIG. 11, RGD presenting nanofiber provided more favorable environment to support self-renewal and proliferation of murine embryonic stem cell even in serum-free conditions. Some of murine stem cells cultured on gelatin-coated surface and N-PAN with no RGD motif were differentiated while no differentiation was observed on all nanofiber surface presenting RGD motif.

Figure 12:
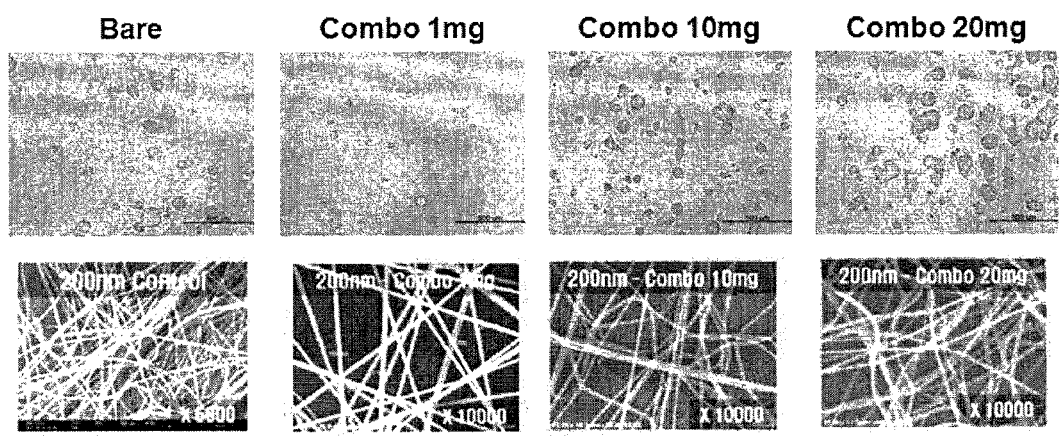
FIG. 12 represents the effect of biochemical cues on self-renewal of murine embryonic stem cell.

Example 11. Effect of Biochemically Defined Nanofibrous Matrix on Embryonic Stem Cell To investigate the surface density of integrin binding motif on the same nanofiber surface, PVDF nanofiber having 200 nm diameter but different amount of PHSRN-RGDSP (SEQ ID NO:17). Higher PHSRN-RGDSP (SEQ ID NO:17) density showed more favorable environment to support self-renewal and proliferation of murine embryonic stem cell (FIG. 12).

Example 12. Effect of Physically Defined Nanofibrous Matrix on Embryonic Stem Cell To investigate the effect of fiber diameter on stem cell fate, two different nanofiber matrix having 200 nm and 700 nm, respectively, were prepared with the same procedure set forth in Example 1. The amount of PHSRN-RGDSP (SEQ ID NO:17) was fixed at 10 mg.

Murine embryonic stem cells were cultured on the nanofiber surface with the same procedure as set forth in Example 3.

The effect of nanofiber diameter on the self-renewal and proliferation was assessed and characterized by expression of markers such as Oct-4 and Nanog.

Expression levels of SSEA-4 and Nanog, the established markers in murine embryonic stem cell, are assessed by immunofluorescence. Cells are harvested as single cell suspensions using trypsin or trypLE express, filtered through a 40 μm sieve (BD) fixed, permeabilized and incubated with primary antibodies to SSEA-4 (1:1000 dilution, Santa Cruz), Nanog (1:50 dilution, Santa Cruz), Oct4 (1:1000 dilution, Santa Cruz).

Figure 13A:
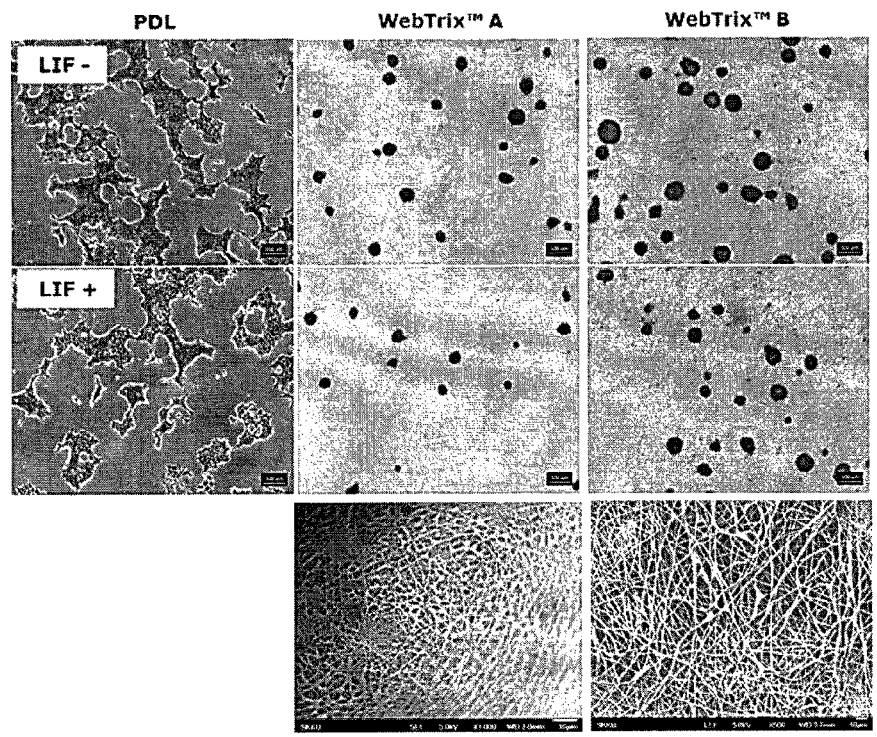
FIGS. 13A-13C represent the effect of physical cues on self-renewal of murine embryonic stem cell.
Figure 13B:
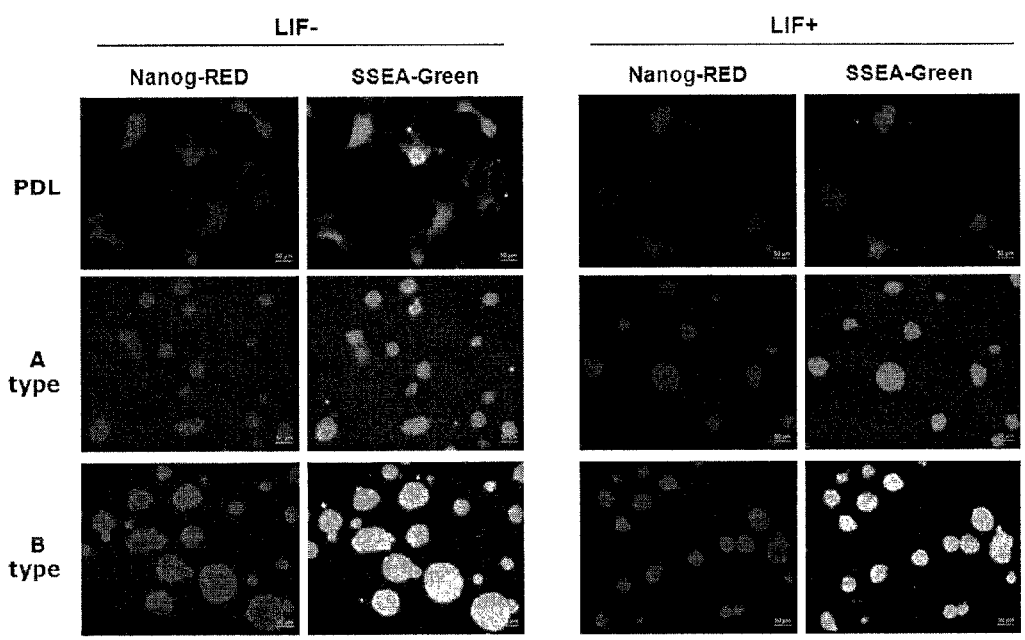
Figure 13C:
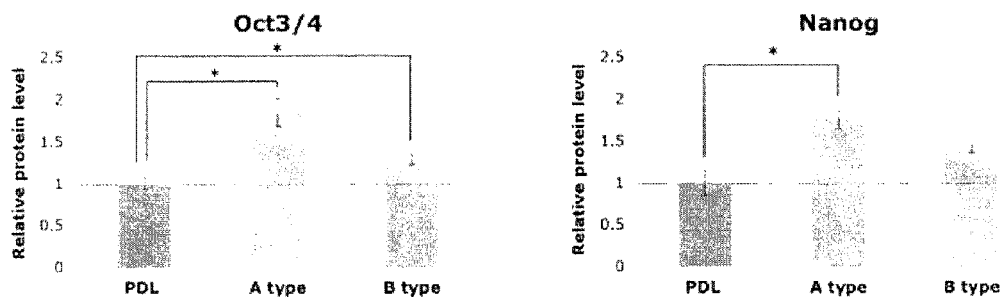

The smaller diameter supported stemness maintenance while the larger diameter supported proliferation of murine embryonic stem cell as evidenced by the expression level of these markers (FIGS. 13B and 13C). Murine embryonic stem cell cultured on nanofiber matrix with 200 nm diameter expressed stem cell markers 1.5 times higher than those on nanofiber matrix with 700 nm (FIG. 13C) but stem cell proliferation was more efficient on the nanofiber matrix with 700 nm than nanofiber with 200 nm.

Example 13. Effect of Physically Defined Nanofibrous Matrix on Human-Induced Pluripotent Stem Cell To investigate the effect of α5β1 binding motif, PHSRN-RGDSP (SEQ ID NO:17), on the self-renewal and proliferation of human-induced pluripotent stem cell, the same test was conducted as set forth in Example 12. Human-induced pluripotent stem cells (Lonza) were cultured on the nanofibrous matrix presenting PHSRN-RGDSP (SEQ ID NO:17) in serum-free conditions. As positive controls, Matrigel™ (BD Bioscience) and PHSRN-RGDSP (SEQ ID NO:17)-coated microwell plate were used for comparison.

Figure 14:
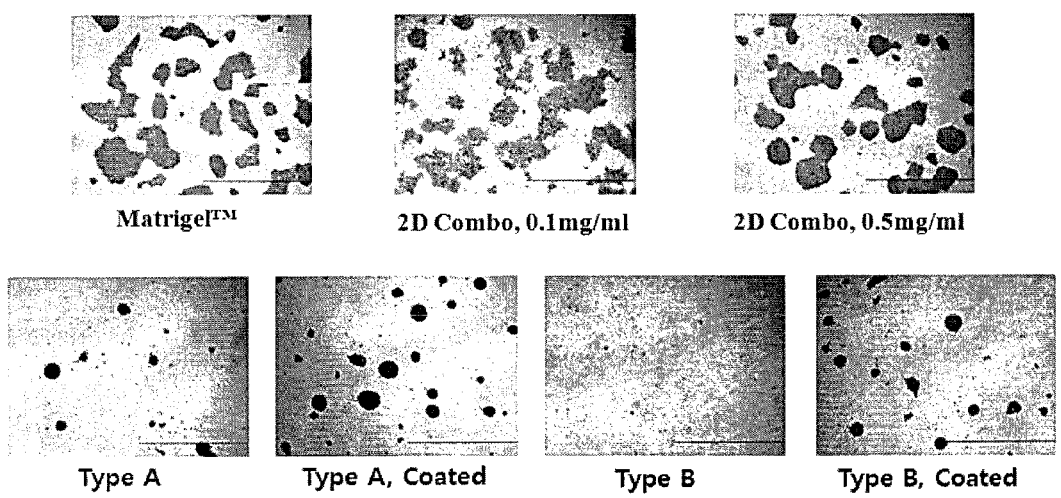
FIG. 14 represents the effect of biochemically and physically defined nanofibrous microenvironment on self-renewal of human-induced pluripotent stem cell.

Morphological and AP staining analysis showed the nanofibrous matrix presenting PHSRN-RGDSP (SEQ ID NO:17) supported self-renewal and proliferation of human-induced stem cell as it did in murine embryonic stem cell culture (FIG. 14). As similar to that of murine embryonic stem cell, smaller diameter (Type A) provided more favorable environment to support stemness of human-induced pluripotent stem cell based on the morphological and AP staining analysis.

What is claimed is:

1. A microenvironment comprising:
   an electroprocessed composition comprising a structure polymer selected from the group consisting of polyvinylidene fluoride (PVDF) and polyacrylonitrile (PAN), and presenting RGD and PHSRN-RGDSP (SEQ ID NO:17) to regulate cellular behavior.

2. The microenvironment of claim 1, wherein the cellular behavior is selected from the group consisting of cell adhesion, cell migration, cell growth, cell differentiation, and any combination thereof.

3. The microenvironment of claim 1, wherein the electroprocessed composition is an electroprocessable biofunctional composition.

4. A method of making an extracellular microenvironment array, wherein the method comprises:
   (a) obtaining an electroprocessable biofunctional composition;
   (b) placing the electroprocessable biofunctional composition on a solid support in a pattern; and
   (c) electroprocessing the electroprocessable biofunctional composition to obtain the extracellular microenvironment array,
   wherein the electroprocessable biofunctional composition presents RGD and PHSRN-RGDSP (SEQ ID NO:17) for regulating cellular behavior.

5. The method according to claim 4, wherein the electroprocessable biofunctional composition presents at least one hydrophilic component that regulates cellular behavior.

6. The method according to claim 5, wherein the cellular behavior is selected from the group consisting of cell adhesion, cell migration, cell growth, cell differentiation, and any combination thereof.

7. A method of making an extracellular microenvironment array, the method comprising:
   electroprocessing an electroprocessable biofunctional composition placed onto a solid support in a pattern so as to obtain an extracellular microenvironment array,
   wherein the electroprocessable biofunctional composition presents RGD and PHSRN-RGDSP (SEQ ID NO:17) that regulates cellular behavior.

8. The method according to claim 7, wherein the cellular behavior is selected from the group consisting of cell adhesion, cell migration, cell growth, cell differentiation, and any combination thereof.

* * * * *

```
                        SEQUENCE LISTING

<160> NUMBER OF SEQ ID NOS: 78

<210> SEQ ID NO 1
<211> LENGTH: 10
<212> TYPE: PRT
<213> ORGANISM: Artificial Sequence
<220> FEATURE:
<223> OTHER INFORMATION: model peptide of the tandem repeat decapeptide
      derived from foot protein 1 (FP-1, Mytilus edulis)

<400> SEQUENCE: 1

Ala Lys Pro Ser Tyr Pro Pro Thr Tyr Lys
1               5                   10

<210> SEQ ID NO 2
<211> LENGTH: 20
<212> TYPE: PRT
<213> ORGANISM: Artificial Sequence
<220> FEATURE:
<223> OTHER INFORMATION: 2 times repeated sequence derived from foot
      protein 1 (FP-1, Mytilus edulis)

<400> SEQUENCE: 2

Ala Lys Pro Ser Tyr Pro Pro Thr Tyr Lys Ala Lys Pro Ser Tyr Pro
1               5                   10                  15

Pro Thr Tyr Lys
            20

<210> SEQ ID NO 3
<211> LENGTH: 60
<212> TYPE: PRT
<213> ORGANISM: Artificial Sequence
<220> FEATURE:
<223> OTHER INFORMATION: 6 times repeated sequence derived from foot
      protein 1 (FP-1, Mytilus edulis)

<400> SEQUENCE: 3

Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
            20                  25                  30

Pro Ser Tyr Pro Pro Thr Tyr Lys Ala Lys Pro Ser Tyr Pro Pro Thr
        35                  40                  45

Tyr Lys Ala Lys Pro Ser Tyr Pro Pro Thr Tyr Lys
    50                  55                  60

<210> SEQ ID NO 4
<211> LENGTH: 39
<212> TYPE: PRT
<213> ORGANISM: Artificial Sequence
```

```
<220> FEATURE:
<223> OTHER INFORMATION: partial sequence of foot protein type 2 (FP-2,
      Mytilus californianus)

<400> SEQUENCE: 4

Glu Val His Ala Cys Lys Pro Asn Pro Cys Lys Asn Asn Gly Arg Cys
1               5                   10                  15

Tyr Pro Asp Gly Lys Thr Gly Tyr Lys Cys Lys Cys Val Gly Gly Tyr
            20                  25                  30

Ser Gly Pro Thr Cys Ala Cys
        35

<210> SEQ ID NO 5
<211> LENGTH: 52
<212> TYPE: PRT
<213> ORGANISM: Artificial Sequence
<220> FEATURE:
<223> OTHER INFORMATION: Foot protein type 3 (FP-3, Mytilus edulis)

<400> SEQUENCE: 5

Ala Asp Tyr Tyr Gly Pro Lys Tyr Gly Pro Pro Arg Arg Tyr Gly Gly
1               5                   10                  15

Gly Asn Tyr Asn Arg Tyr Gly Gly Ser Arg Arg Tyr Gly Gly Tyr Lys
            20                  25                  30

Gly Trp Asn Asn Gly Trp Lys Arg Gly Arg Trp Gly Arg Lys Tyr Tyr
        35                  40                  45

Glu Phe Glu Phe
    50

<210> SEQ ID NO 6
<211> LENGTH: 46
<212> TYPE: PRT
<213> ORGANISM: Artificial Sequence
<220> FEATURE:
<223> OTHER INFORMATION: Foot protein type 3 (FP-3, Mytilus
      galloprovincialis : mgfp-3A)

<400> SEQUENCE: 6

Ala Asp Tyr Tyr Gly Pro Lys Tyr Gly Pro Pro Arg Arg Tyr Gly Gly
1               5                   10                  15

Gly Asn Tyr Asn Arg Tyr Gly Arg Arg Tyr Gly Gly Tyr Lys Gly Trp
            20                  25                  30

Asn Asn Gly Trp Lys Arg Gly Arg Trp Gly Arg Lys Tyr Tyr
        35                  40                  45

<210> SEQ ID NO 7
<211> LENGTH: 60
<212> TYPE: PRT
<213> ORGANISM: Artificial Sequence
<220> FEATURE:
<223> OTHER INFORMATION: partial sequence from foot protein type 4
      (Mytilus californianus)

<400> SEQUENCE: 7

Gly His Val His Arg His Arg Val Leu His Lys His Val Asn His
1               5                   10                  15

Arg Val Leu His Lys His Leu His Lys His Gln Val Leu His Gly His
            20                  25                  30

Val His Arg His Gln Val Leu His Lys His Val His Asn His Arg Val
        35                  40                  45

Leu His Lys His Leu His Lys His Gln Val Leu His
    50                  55                  60
```

<210> SEQ ID NO 8
<211> LENGTH: 75
<212> TYPE: PRT
<213> ORGANISM: Artificial Sequence
<220> FEATURE:
<223> OTHER INFORMATION: Foot protein type5 (FP-5, Mytilus edulis)

<400> SEQUENCE: 8

Ser Ser Glu Glu Tyr Lys Gly Gly Tyr Tyr Pro Gly Asn Ala Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Tyr Tyr Tyr Lys Tyr Lys
        35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Ser Ser
65                  70                  75

<210> SEQ ID NO 9
<211> LENGTH: 76
<212> TYPE: PRT
<213> ORGANISM: Artificial Sequence
<220> FEATURE:
<223> OTHER INFORMATION: Foot protein 5 (FP-5, Mytilus edulis)

<400> SEQUENCE: 9

Ser Ser Glu Glu Tyr Lys Gly Gly Tyr Tyr Pro Gly Asn Thr Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Tyr Tyr Tyr Lys Tyr Lys
        35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Ser Ser
65                  70                  75

<210> SEQ ID NO 10
<211> LENGTH: 71
<212> TYPE: PRT
<213> ORGANISM: Artificial Sequence
<220> FEATURE:
<223> OTHER INFORMATION: Foot protein 5 (FP-5, Mytilus coruscus)

<400> SEQUENCE: 10

Tyr Asp Asp Tyr Ser Asp Gly Tyr Tyr Pro Gly Ser Ala Tyr Asn Tyr
1               5                   10                  15

Pro Ser Gly Ser His Trp His Gly His Gly Tyr Lys Gly Lys Tyr Tyr
            20                  25                  30

Gly Lys Gly Lys Lys Tyr Tyr Tyr Lys Phe Lys Arg Thr Gly Lys Tyr
        35                  40                  45

Lys Tyr Leu Lys Lys Ala Arg Lys Tyr His Arg Lys Gly Tyr Lys Lys
    50                  55                  60

His Tyr Gly Gly Ser Ser Ser
65                  70

<210> SEQ ID NO 11
<211> LENGTH: 76

```
<212> TYPE: PRT
<213> ORGANISM: Artificial Sequence
<220> FEATURE:
<223> OTHER INFORMATION: mussel adhesive protein foot protein type5 from
      (Mytilus galloprovincialis)

<400> SEQUENCE: 11

Ser Ser Glu Glu Tyr Lys Gly Gly Tyr Tyr Pro Gly Asn Thr Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Tyr Lys Tyr Lys
        35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Ser Ser
65                  70                  75

<210> SEQ ID NO 12
<211> LENGTH: 99
<212> TYPE: PRT
<213> ORGANISM: Artificial Sequence
<220> FEATURE:
<223> OTHER INFORMATION: mussel adhesive protein foot protein type 6

<400> SEQUENCE: 12

Gly Gly Gly Asn Tyr Arg Gly Tyr Cys Ser Asn Lys Gly Cys Arg Ser
1               5                   10                  15

Gly Tyr Ile Phe Tyr Asp Asn Arg Gly Phe Cys Lys Tyr Gly Ser Ser
            20                  25                  30

Ser Tyr Lys Tyr Asp Cys Gly Asn Tyr Ala Gly Cys Cys Leu Pro Arg
        35                  40                  45

Asn Pro Tyr Gly Arg Val Lys Tyr Tyr Cys Thr Lys Lys Tyr Ser Cys
    50                  55                  60

Pro Asp Asp Phe Tyr Tyr Tyr Asn Asn Lys Gly Tyr Tyr Tyr Tyr Asn
65                  70                  75                  80

Asp Lys Asp Tyr Phe Asn Cys Gly Ser Tyr Asn Gly Cys Cys Leu Arg
                85                  90                  95

Ser Gly Tyr

<210> SEQ ID NO 13
<211> LENGTH: 194
<212> TYPE: PRT
<213> ORGANISM: Artificial Sequence
<220> FEATURE:
<223> OTHER INFORMATION: hybrid mussel adhesive protein (FP-151, MEFP-5
      based: Kollodis)

<400> SEQUENCE: 13

Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
            20                  25                  30

Pro Ser Tyr Pro Pro Thr Tyr Lys Ala Lys Pro Ser Tyr Pro Pro Thr
        35                  40                  45

Tyr Lys Ala Lys Pro Ser Tyr Pro Pro Thr Tyr Lys Ser Ser Glu Glu
    50                  55                  60

Tyr Lys Gly Gly Tyr Tyr Pro Gly Asn Ala Tyr His Tyr His Ser Gly
65                  70                  75                  80
```

```
Gly Ser Tyr His Gly Ser Gly Tyr His Gly Gly Tyr Lys Gly Lys Tyr
                85                  90                  95

Tyr Gly Lys Ala Lys Lys Tyr Tyr Lys Tyr Lys Asn Ser Gly Lys
            100                 105                 110

Tyr Lys Tyr Leu Lys Lys Ala Arg Lys Tyr His Arg Lys Gly Tyr Lys
            115                 120                 125

Tyr Tyr Gly Gly Ser Ser Ala Lys Pro Ser Tyr Pro Pro Thr Tyr Lys
            130                 135                 140

Ala Lys Pro Ser Tyr Pro Pro Thr Tyr Lys Ala Lys Pro Ser Tyr Pro
145                 150                 155                 160

Pro Thr Tyr Lys Ala Lys Pro Ser Tyr Pro Pro Thr Tyr Lys Ala Lys
            165                 170                 175

Pro Ser Tyr Pro Pro Thr Tyr Lys Ala Lys Pro Ser Tyr Pro Pro Thr
            180                 185                 190

Tyr Lys

<210> SEQ ID NO 14
<211> LENGTH: 196
<212> TYPE: PRT
<213> ORGANISM: Artificial Sequence
<220> FEATURE:
<223> OTHER INFORMATION: hybrid mussel adhesive protein (FP-151, MGFP-5
      based)

<400> SEQUENCE: 14

Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
            20                  25                  30

Pro Ser Tyr Pro Pro Thr Tyr Lys Ala Lys Pro Ser Tyr Pro Pro Thr
            35                  40                  45

Tyr Lys Ala Lys Pro Ser Tyr Pro Pro Thr Tyr Lys Ser Ser Glu Glu
        50                  55                  60

Tyr Lys Gly Gly Tyr Tyr Pro Gly Asn Thr Tyr His Tyr His Ser Gly
65                  70                  75                  80

Gly Ser Tyr His Gly Ser Gly Tyr His Gly Gly Tyr Lys Gly Lys Tyr
                85                  90                  95

Tyr Gly Lys Ala Lys Lys Tyr Tyr Lys Tyr Lys Asn Ser Gly Lys
            100                 105                 110

Tyr Lys Tyr Leu Lys Lys Ala Arg Lys Tyr His Arg Lys Gly Tyr Lys
            115                 120                 125

Lys Tyr Tyr Gly Gly Gly Ser Ser Ala Lys Pro Ser Tyr Pro Pro Thr
        130                 135                 140

Tyr Lys Ala Lys Pro Ser Tyr Pro Pro Thr Tyr Lys Ala Lys Pro Ser
145                 150                 155                 160

Tyr Pro Pro Thr Tyr Lys Ala Lys Pro Ser Tyr Pro Pro Thr Tyr Lys
            165                 170                 175

Ala Lys Pro Ser Tyr Pro Pro Thr Tyr Lys Ala Lys Pro Ser Tyr Pro
            180                 185                 190

Pro Thr Tyr Lys
195

<210> SEQ ID NO 15
<211> LENGTH: 3
<212> TYPE: PRT
<213> ORGANISM: Artificial Sequence
<220> FEATURE:
```

```
<223> OTHER INFORMATION: Fibronectin-derived peptide (RGD)

<400> SEQUENCE: 15

Arg Gly Asp
1

<210> SEQ ID NO 16
<211> LENGTH: 6
<212> TYPE: PRT
<213> ORGANISM: Artificial Sequence
<220> FEATURE:
<223> OTHER INFORMATION: Fibronectin-derived peptide (GRGDSP)

<400> SEQUENCE: 16

Gly Arg Gly Asp Ser Pro
1               5

<210> SEQ ID NO 17
<211> LENGTH: 10
<212> TYPE: PRT
<213> ORGANISM: Artificial Sequence
<220> FEATURE:
<223> OTHER INFORMATION: Fibronectin-derived peptide (PHSRN-RGDSP)

<400> SEQUENCE: 17

Pro His Ser Arg Asn Arg Gly Asp Ser Pro
1               5                   10

<210> SEQ ID NO 18
<211> LENGTH: 9
<212> TYPE: PRT
<213> ORGANISM: Artificial Sequence
<220> FEATURE:
<223> OTHER INFORMATION: Fibronectin-derived peptide (SPPRRARVT)

<400> SEQUENCE: 18

Ser Pro Pro Arg Arg Ala Arg Val Thr
1               5

<210> SEQ ID NO 19
<211> LENGTH: 8
<212> TYPE: PRT
<213> ORGANISM: Artificial Sequence
<220> FEATURE:
<223> OTHER INFORMATION: Fibronectin-derived peptide (WQPPRARI)

<400> SEQUENCE: 19

Trp Gln Pro Pro Arg Ala Arg Ile
1               5

<210> SEQ ID NO 20
<211> LENGTH: 15
<212> TYPE: PRT
<213> ORGANISM: Artificial Sequence
<220> FEATURE:
<223> OTHER INFORMATION: Fibronectin-derived peptide (KNNQKSEPLIGRKKT)

<400> SEQUENCE: 20

Lys Asn Asn Gln Lys Ser Glu Pro Leu Ile Gly Arg Lys Lys Thr
1               5                   10                  15

<210> SEQ ID NO 21
<211> LENGTH: 12
<212> TYPE: PRT
<213> ORGANISM: Artificial Sequence
<220> FEATURE:
<223> OTHER INFORMATION: Laminin-derived peptide (RKRLQVQLSIRT)
```

```
<400> SEQUENCE: 21

Arg Lys Arg Leu Gln Val Gln Leu Ser Ile Arg Thr
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Laminin-derived peptide (GKNTGDHFVLYM)

<400> SEQUENCE: 22

Gly Lys Asn Thr Gly Asp His Phe Val Leu Tyr Met
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Laminin-derived peptide (VVSLYNFEQTFML)

<400> SEQUENCE: 23

Val Val Ser Leu Tyr Asn Phe Glu Gln Thr Phe Met Leu
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Laminin-derived peptide (RFDQELRLVSYN)

<400> SEQUENCE: 24

Arg Phe Asp Gln Glu Leu Arg Leu Val Ser Tyr Asn
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Laminin-derived peptide (RLVSYSGVLFFLK)

<400> SEQUENCE: 25

Arg Leu Val Ser Tyr Ser Gly Val Leu Phe Phe Leu Lys
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Laminin-derived peptide (ASKAIQVFLLGG)

<400> SEQUENCE: 26

Ala Ser Lys Ala Ile Gln Val Phe Leu Leu Gly Gly
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Laminin-derived peptide (VLVRVERATVFS)
```

```
<400> SEQUENCE: 27

Thr His Arg Pro Pro Met Trp Ser Pro Val Trp Pro
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Laminin-derived peptide (TVFSVDQDNMLE)

<400> SEQUENCE: 28

Thr Val Phe Ser Val Asp Gln Asp Asn Met Leu Glu
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Laminin-derived peptide (RLRGPQRVFDLH)

<400> SEQUENCE: 29

Arg Leu Arg Gly Pro Gln Arg Val Phe Asp Leu His
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Laminin-derived peptide (FDLHQNMGSVN)

<400> SEQUENCE: 30

Phe Asp Leu His Gln Asn Met Gly Ser Val Asn
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Laminin-derived peptide (QQNLGSVNVSTG)

<400> SEQUENCE: 31

Gln Gln Asn Leu Gly Ser Val Asn Val Ser Thr Gly
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Laminin-derived (SRATAQKVSRRS)

<400> SEQUENCE: 32

Ser Arg Ala Thr Ala Gln Lys Val Ser Arg Arg Ser
1               5                   10

<210> SEQ ID NO 33
<211> LENGTH: 16
<212> TYPE: PRT
<213> ORGANISM: Artificial Sequence
<220> FEATURE:
<223> OTHER INFORMATION: FGF-derived peptide (ANRYLAMKEDGRLLAS)

<400> SEQUENCE: 33
```

```
Ala Asn Arg Tyr Leu Ala Met Lys Glu Asp Gly Arg Leu Leu Ala Ser
1               5                   10                  15
```

<210> SEQ ID NO 34
<211> LENGTH: 11
<212> TYPE: PRT
<213> ORGANISM: Artificial Sequence
<220> FEATURE:
<223> OTHER INFORMATION: FGF-derived peptide (HFKDPKRLYCK)

<400> SEQUENCE: 34

```
His Phe Lys Asp Pro Lys Arg Leu Tyr Cys Lys
1               5                   10
```

<210> SEQ ID NO 35
<211> LENGTH: 8
<212> TYPE: PRT
<213> ORGANISM: Artificial Sequence
<220> FEATURE:
<223> OTHER INFORMATION: FGF-derived peptide (FLPMSAKS)

<400> SEQUENCE: 35

```
Phe Leu Pro Met Ser Ala Lys Ser
1               5
```

<210> SEQ ID NO 36
<211> LENGTH: 8
<212> TYPE: PRT
<213> ORGANISM: Artificial Sequence
<220> FEATURE:
<223> OTHER INFORMATION: FGF-derived peptide (KTGPGQKA)

<400> SEQUENCE: 36

```
Lys Thr Gly Pro Gly Gln Lys Ala
1               5
```

<210> SEQ ID NO 37
<211> LENGTH: 12
<212> TYPE: PRT
<213> ORGANISM: Artificial Sequence
<220> FEATURE:
<223> OTHER INFORMATION: TGF-derived peptide (LTGKNFPMFHRN)

<400> SEQUENCE: 37

```
Leu Thr Gly Lys Asn Phe Pro Met Phe His Arg Asn
1               5                   10
```

<210> SEQ ID NO 38
<211> LENGTH: 12
<212> TYPE: PRT
<213> ORGANISM: Artificial Sequence
<220> FEATURE:
<223> OTHER INFORMATION: TGF-derived peptide (MHRMPSFLPTTL)

<400> SEQUENCE: 38

```
Met His Arg Met Pro Ser Phe Leu Pro Thr Thr Leu
1               5                   10
```

<210> SEQ ID NO 39
<211> LENGTH: 20
<212> TYPE: PRT
<213> ORGANISM: Artificial Sequence
<220> FEATURE:
<223> OTHER INFORMATION: WNT-derived peptide (LCCGRGHRTRTQRVTERCNC)

<400> SEQUENCE: 39

```
Leu Cys Cys Gly Arg Gly His Arg Thr Arg Thr Gln Arg Val Thr Glu
1               5                   10                  15

Arg Cys Asn Cys
            20

<210> SEQ ID NO 40
<211> LENGTH: 20
<212> TYPE: PRT
<213> ORGANISM: Artificial Sequence
<220> FEATURE:
<223> OTHER INFORMATION: WNT-derived peptide (LGTQGRLCNKTSEGMDGCEL)

<400> SEQUENCE: 40

Leu Gly Thr Gln Gly Arg Leu Cys Asn Lys Thr Ser Glu Gly Met Asp
1               5                   10                  15

Gly Cys Glu Leu
            20

<210> SEQ ID NO 41
<211> LENGTH: 10
<212> TYPE: PRT
<213> ORGANISM: Artificial Sequence
<220> FEATURE:
<223> OTHER INFORMATION: LIF-derived peptide (IVPLLLLVLH)

<400> SEQUENCE: 41

Ile Val Pro Leu Leu Leu Leu Val Leu His
1               5                   10

<210> SEQ ID NO 42
<211> LENGTH: 18
<212> TYPE: PRT
<213> ORGANISM: Artificial Sequence
<220> FEATURE:
<223> OTHER INFORMATION: LIF-derived peptide (YTAQGEPFPNNVEKLCAP)

<400> SEQUENCE: 42

Tyr Thr Ala Gln Gly Glu Pro Phe Pro Asn Asn Val Glu Lys Leu Cys
1               5                   10                  15

Ala Pro

<210> SEQ ID NO 43
<211> LENGTH: 6
<212> TYPE: PRT
<213> ORGANISM: Artificial Sequence
<220> FEATURE:
<223> OTHER INFORMATION: Fibronectin-derived peptide (KLDAPT)

<400> SEQUENCE: 43

Lys Leu Asp Ala Pro Thr
1               5

<210> SEQ ID NO 44
<211> LENGTH: 9
<212> TYPE: PRT
<213> ORGANISM: Artificial Sequence
<220> FEATURE:
<223> OTHER INFORMATION: Fibronectin-derived peptide (EILDVPSTT)

<400> SEQUENCE: 44

Glu Ile Leu Asp Val Pro Ser Thr Thr
1               5

<210> SEQ ID NO 45
<211> LENGTH: 12
```

```
<212> TYPE: PRT
<213> ORGANISM: Artificial Sequence
<220> FEATURE:
<223> OTHER INFORMATION: Laminin-derived peptide (TWYKIAFQRNRK)

<400> SEQUENCE: 45

Thr Trp Tyr Lys Ile Ala Phe Gln Arg Asn Arg Lys
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Laminin-derived peptide (NRWHSIYITRFG)

<400> SEQUENCE: 46

Asn Arg Trp His Ser Ile Tyr Ile Thr Arg Phe Gly
1               5                   10

<210> SEQ ID NO 47
<211> LENGTH: 4
<212> TYPE: PRT
<213> ORGANISM: Artificial Sequence
<220> FEATURE:
<223> OTHER INFORMATION: Fibronectin-derived peptide (REDV)

<400> SEQUENCE: 47

Arg Glu Asp Val
1

<210> SEQ ID NO 48
<211> LENGTH: 6
<212> TYPE: PRT
<213> ORGANISM: Artificial Sequence
<220> FEATURE:
<223> OTHER INFORMATION: cadherin-derived peptide (SHAVSS)

<400> SEQUENCE: 48

Ser His Ala Val Ser Ser
1               5

<210> SEQ ID NO 49
<211> LENGTH: 10
<212> TYPE: PRT
<213> ORGANISM: Artificial Sequence
<220> FEATURE:
<223> OTHER INFORMATION: cadherin-derived peptide (LFSHAVSSNG)

<400> SEQUENCE: 49

Leu Phe Ser His Ala Val Ser Ser Asn Gly
1               5                   10

<210> SEQ ID NO 50
<211> LENGTH: 6
<212> TYPE: PRT
<213> ORGANISM: Artificial Sequence
<220> FEATURE:
<223> OTHER INFORMATION: cadherin-derived peptide (ADTPPV)

<400> SEQUENCE: 50

Ala Asp Thr Pro Pro Val
1               5

<210> SEQ ID NO 51
<211> LENGTH: 5
<212> TYPE: PRT
```

```
<213> ORGANISM: Artificial Sequence
<220> FEATURE:
<223> OTHER INFORMATION: cadherin-derived peptide (DQNDN)

<400> SEQUENCE: 51

Asp Gln Asn Asp Asn
1               5

<210> SEQ ID NO 52
<211> LENGTH: 5
<212> TYPE: PRT
<213> ORGANISM: Artificial Sequence
<220> FEATURE:
<223> OTHER INFORMATION: cadherin-derived peptide (HAVDI)

<400> SEQUENCE: 52

His Ala Val Asp Ile
1               5

<210> SEQ ID NO 53
<211> LENGTH: 10
<212> TYPE: PRT
<213> ORGANISM: Artificial Sequence
<220> FEATURE:
<223> OTHER INFORMATION: cadherin-derived peptide (LRAHAVDING)

<400> SEQUENCE: 53

Leu Arg Ala His Ala Val Asp Ile Asn Gly
1               5                   10

<210> SEQ ID NO 54
<211> LENGTH: 6
<212> TYPE: PRT
<213> ORGANISM: Artificial Sequence
<220> FEATURE:
<223> OTHER INFORMATION: derived peptide

<400> SEQUENCE: 54

Lys Gly His Arg Gly Phe
1               5

<210> SEQ ID NO 55
<211> LENGTH: 12
<212> TYPE: PRT
<213> ORGANISM: Artificial Sequence
<220> FEATURE:
<223> OTHER INFORMATION: derived peptide

<400> SEQUENCE: 55

Thr Ala Gly Ser Cys Leu Arg Lys Phe Ser Thr Met
1               5                   10

<210> SEQ ID NO 56
<211> LENGTH: 13
<212> TYPE: PRT
<213> ORGANISM: Artificial Sequence
<220> FEATURE:
<223> OTHER INFORMATION: derived peptide

<400> SEQUENCE: 56

Gly Glu Phe Tyr Phe Asp Leu Arg Leu Lys Gly Asp Lys
1               5                   10

<210> SEQ ID NO 57
<211> LENGTH: 15
<212> TYPE: PRT
<213> ORGANISM: Artificial Sequence
```

```
<220> FEATURE:
<223> OTHER INFORMATION: derived peptide

<400> SEQUENCE: 57

Thr Ala Ile Pro Ser Cys Pro Glu Gly Thr Val Pro Leu Tyr Ser
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: derived peptide

<400> SEQUENCE: 58

Tyr Arg Val Arg Val Thr Pro Lys Glu Lys Thr Gly Pro Met Lys Glu
1               5                   10                  15

<210> SEQ ID NO 59
<211> LENGTH: 11
<212> TYPE: PRT
<213> ORGANISM: Artificial Sequence
<220> FEATURE:
<223> OTHER INFORMATION: derived peptide

<400> SEQUENCE: 59

Lys Tyr Ile Leu Arg Trp Arg Pro Lys Asn Ser
1               5                   10

<210> SEQ ID NO 60
<211> LENGTH: 11
<212> TYPE: PRT
<213> ORGANISM: Artificial Sequence
<220> FEATURE:
<223> OTHER INFORMATION: derived peptide

<400> SEQUENCE: 60

Lys Pro Asp Val Arg Ser Tyr Thr Ile Thr Gly
1               5                   10

<210> SEQ ID NO 61
<211> LENGTH: 9
<212> TYPE: PRT
<213> ORGANISM: Artificial Sequence
<220> FEATURE:
<223> OTHER INFORMATION: derived peptide

<400> SEQUENCE: 61

Ala Thr Glu Thr Thr Ile Thr Ile Ser
1               5

<210> SEQ ID NO 62
<211> LENGTH: 19
<212> TYPE: PRT
<213> ORGANISM: Artificial Sequence
<220> FEATURE:
<223> OTHER INFORMATION: derived peptide

<400> SEQUENCE: 62

Tyr Glu Lys Pro Gly Ser Pro Pro Arg Glu Val Val Pro Arg Pro Arg
1               5                   10                  15

Pro Gly Val

<210> SEQ ID NO 63
<211> LENGTH: 12
<212> TYPE: PRT
```

```
<213> ORGANISM: Artificial Sequence
<220> FEATURE:
<223> OTHER INFORMATION: derived peptide

<400> SEQUENCE: 63

Ser Ile Asn Asn Thr Ala Val Met Gln Arg Leu Thr
1               5                   10

<210> SEQ ID NO 64
<211> LENGTH: 7
<212> TYPE: PRT
<213> ORGANISM: Artificial Sequence
<220> FEATURE:
<223> OTHER INFORMATION: derived peptide

<400> SEQUENCE: 64

Arg Tyr Val Val Leu Pro Arg
1               5

<210> SEQ ID NO 65
<211> LENGTH: 6
<212> TYPE: PRT
<213> ORGANISM: Artificial Sequence
<220> FEATURE:
<223> OTHER INFORMATION: derived peptide

<400> SEQUENCE: 65

Gly Ile Ile Phe Phe Leu
1               5

<210> SEQ ID NO 66
<211> LENGTH: 12
<212> TYPE: PRT
<213> ORGANISM: Artificial Sequence
<220> FEATURE:
<223> OTHER INFORMATION: derived peptide

<400> SEQUENCE: 66

Ala Asn Val Thr His Leu Leu Ile Arg Ala Asn Tyr
1               5                   10

<210> SEQ ID NO 67
<211> LENGTH: 12
<212> TYPE: PRT
<213> ORGANISM: Artificial Sequence
<220> FEATURE:
<223> OTHER INFORMATION: derived peptide

<400> SEQUENCE: 67

Val Leu Val Arg Val Glu Arg Ala Thr Val Phe Ser
1               5                   10

<210> SEQ ID NO 68
<211> LENGTH: 17
<212> TYPE: PRT
<213> ORGANISM: Artificial Sequence
<220> FEATURE:
<223> OTHER INFORMATION: derived peptide

<400> SEQUENCE: 68

Arg Ile Gln Asn Leu Leu Lys Ile Thr Asn Leu Arg Ile Lys Phe Val
1               5                   10                  15

Lys

<210> SEQ ID NO 69
<211> LENGTH: 7
```

```
<212> TYPE: PRT
<213> ORGANISM: Artificial Sequence
<220> FEATURE:
<223> OTHER INFORMATION: derived peptide

<400> SEQUENCE: 69

Phe His Arg Arg Ile Lys Ala
1               5

<210> SEQ ID NO 70
<211> LENGTH: 9
<212> TYPE: PRT
<213> ORGANISM: Artificial Sequence
<220> FEATURE:
<223> OTHER INFORMATION: derived peptide

<400> SEQUENCE: 70

Phe Arg His Arg Asn Arg Lys Gly Tyr
1               5

<210> SEQ ID NO 71
<211> LENGTH: 4
<212> TYPE: PRT
<213> ORGANISM: Artificial Sequence
<220> FEATURE:
<223> OTHER INFORMATION: derived peptide

<400> SEQUENCE: 71

Lys Arg Ser Arg
1

<210> SEQ ID NO 72
<211> LENGTH: 12
<212> TYPE: PRT
<213> ORGANISM: Artificial Sequence
<220> FEATURE:
<223> OTHER INFORMATION: derived peptide

<400> SEQUENCE: 72

Gly Pro Gly Val Val Val Val Glu Arg Gln Tyr Ile
1               5                   10

<210> SEQ ID NO 73
<211> LENGTH: 8
<212> TYPE: PRT
<213> ORGANISM: Artificial Sequence
<220> FEATURE:
<223> OTHER INFORMATION: derived peptide

<400> SEQUENCE: 73

Pro His Ser Arg Asn Arg Gly Asp
1               5

<210> SEQ ID NO 74
<211> LENGTH: 6
<212> TYPE: PRT
<213> ORGANISM: Artificial Sequence
<220> FEATURE:
<223> OTHER INFORMATION: derived peptide

<400> SEQUENCE: 74

Arg Lys Arg Leu Gln Val
1               5

<210> SEQ ID NO 75
<211> LENGTH: 12
<212> TYPE: PRT
```

```
<213> ORGANISM: Artificial Sequence
<220> FEATURE:
<223> OTHER INFORMATION: derived peptide

<400> SEQUENCE: 75

Lys Ala Phe Asp Ile Thr Tyr Val Arg Leu Lys Phe
1               5                   10

<210> SEQ ID NO 76
<211> LENGTH: 10
<212> TYPE: PRT
<213> ORGANISM: Artificial Sequence
<220> FEATURE:
<223> OTHER INFORMATION: derived peptide

<400> SEQUENCE: 76

Lys Thr Gly Pro Gly Gln Lys Ala Ile Leu
1               5                   10

<210> SEQ ID NO 77
<211> LENGTH: 5
<212> TYPE: PRT
<213> ORGANISM: Artificial Sequence
<220> FEATURE:
<223> OTHER INFORMATION: derived peptide

<400> SEQUENCE: 77

Ile Lys Val Ala Val
1               5

<210> SEQ ID NO 78
<211> LENGTH: 5
<212> TYPE: PRT
<213> ORGANISM: Artificial Sequence
<220> FEATURE:
<223> OTHER INFORMATION: derived peptide

<400> SEQUENCE: 78

Ile Lys Phe Ala Val
1               5
```